US006921496B2

(12) United States Patent
Anderson et al.

(10) Patent No.: US 6,921,496 B2
(45) Date of Patent: Jul. 26, 2005

(54) INORGANIC PARTICLE CONJUGATES

(75) Inventors: George P. Anderson, Lanham, MD (US); Hedi Mattoussi, Alexandria, VA (US); J. Matthew Mauro, Silver Spring, MD (US); Moungi G. Bawendi, Boston, MA (US); Vikram C. Sundar, Stoneham, MA (US)

(73) Assignees: Massachusetts Institute of Technology, Cambridge, MA (US); The United States of Americas as represented by the Secretary of the Navy, Washington, DC (US)

( * ) Notice: Subject to any disclaimer, the term of this patent is extended or adjusted under 35 U.S.C. 154(b) by 513 days.

(21) Appl. No.: 09/811,824

(22) Filed: Mar. 20, 2001

(65) Prior Publication Data

US 2002/0182632 A1 Dec. 5, 2002

Related U.S. Application Data

(60) Provisional application No. 60/190,766, filed on Mar. 20, 2000.

(51) Int. Cl.[7] .......................... C09K 11/54; C12P 21/00
(52) U.S. Cl. ............................... 252/301.6 S; 435/69.7; 435/6; 435/69.1; 435/7.1; 252/301.33; 252/301.36; 436/2; 436/172; 436/546
(58) Field of Search ............................. 435/69.7, 69.1, 435/6, 7.1; 436/172, 546, 2; 252/301.6 S, 301.33, 301.36; 250/459.1; 356/317; 422/82.08

(56) References Cited

U.S. PATENT DOCUMENTS

| | | | |
|---|---|---|---|
| 4,738,932 A | 4/1988 | Yabusaki | |
| 5,262,357 A | 11/1993 | Alivisatos et al. | |
| 5,505,928 A | 4/1996 | Alivisatos et al. | |
| 5,525,377 A | 6/1996 | Gallagher et al. | |
| 5,537,000 A | 7/1996 | Alivisatos et al. | |
| 5,565,324 A | 10/1996 | Still et al. | |
| 5,585,640 A | 12/1996 | Huston et al. | |
| 5,674,698 A | 10/1997 | Zarling et al. | |
| 5,721,099 A | 2/1998 | Still et al. | |
| 5,736,330 A | 4/1998 | Fulton | |
| 5,751,018 A | 5/1998 | Alivisatos et al. | |
| 5,789,162 A | 8/1998 | Dower et al. | |
| 5,985,353 A | 11/1999 | Lawton et al. | |
| 5,990,479 A | 11/1999 | Weiss et al. | |
| 6,114,038 A | 9/2000 | Castro et al. | |
| 6,207,229 B1 | 3/2001 | Bawendi et al. | |
| 6,251,303 B1 | 6/2001 | Bawendi et al. | |
| 6,306,610 B1 * | 10/2001 | Bawendi et al. | ............. 435/7.1 |
| 6,326,144 B1 * | 12/2001 | Bawendi et al. | ............... 435/6 |

FOREIGN PATENT DOCUMENTS

| | | |
|---|---|---|
| EP | 0 990 903 A1 | 4/2000 |
| WO | WO 94/11103 | 5/1994 |
| WO | WO 98/04740 | 2/1998 |
| WO | WO 98/19963 | 5/1998 |
| WO | WO 99/19515 | 4/1999 |
| WO | WO 99/26299 | 6/1999 |
| WO | WO 99/50916 | 10/1999 |
| WO | WO 00/17103 | 3/2000 |
| WO | WO 00/17642 | 3/2000 |
| WO | WO 00/17655 | 3/2000 |
| WO | WO 00/17656 | 3/2000 |
| WO | WO 00/27365 | 5/2000 |
| WO | WO 00/27436 | 5/2000 |
| WO | WO 00/28088 | 5/2000 |
| WO | WO 00/28089 | 5/2000 |
| WO | WO 01/07689 | 2/2001 |

OTHER PUBLICATIONS

Alivisatos, A.P., "Perspectives on the Physical Chemistry of Semicondutor Nanocrystals", J. Phys. Chem., vol. 100, No. 31, pp. 13226–13239, (1996).

Alivisatos, A. P., "Organization of 'naoncrystal molecules' using DNA", Nature, vol. 382, pp. 609–611, (1996).

Baldwin et al., "Synthesis of a Small Molecule Combinatorial Library Encoded with Molecular Tags", J. Am. Chem. Soc., vol. 117, No. 20, pp. 5588–5589, (1995).

Beverloo et al., "Preparation and Microscopic Visualization of Multicolor Luminescent Immunophosphors", Cytometry, vol. 13, No. 6, pp. 561–570, (1992).

Bruchez Jr., M. P., "Luminescent Semconductor Nanocrystals—Intermittent Behavior and Use as Fluorescent Biological Probes", Doctoral Dissertion, University of California, (Jul. 13, 1999).

Bruchez Jr. et al., "Semiconductor Nanocrystals as Fluorescent Biological Labels", Science, vol. 281, pp. 2013–2016, (1998).

Chan et al., "Quantum dot Bioconjugates for Ultrasensitive Nonisotopic Detection", Science, vol. 281, pp. 2016–2018, (1998).

Chee et al., "Accessing Genetic Information with High Density DNA Arrays", Science, vol. 274, No. 5287, pp. 610–614, (1998).

Coffer et al., "Characterization of quantum–confined CdS nanocrystallites stabilized by deoxyribonucleic acid (DNA)", Nanotechnology, vol. 3, pp. 69–76, (1992).

Czarnik, A. W., "Encoding methods for combinatorial chemistry", Curr. Opin. Chemical Biology, vol. 1, pp. 60–66, (1977).

Dabbousi et al., "Electroluminescence from CdSe quantum–dot/polymer composites", Appl. Phys. Lett., vol. 66, No. 11, pp. 1316–1318, (1995).

Egner et al., "Tagging in combinatorial chemistry: the use of coloured and fluorescent beads", Chem. Commun., pp. 735–736, (1997).

(Continued)

Primary Examiner—Jon Weber
Assistant Examiner—Chih-Min Kam
(74) Attorney, Agent, or Firm—Steptoe & Johnson LLP

(57) ABSTRACT

The ionic conjugates include an inorganic particle electrostatically associated with a macromolecule which can interact specifically with predetermined chemical species or biological targets.

29 Claims, 10 Drawing Sheets

OTHER PUBLICATIONS

Fodor, S. P. A., "Techwire", Science, vol. 277, No. 5324, pp. 393–395, (1997).

Jacoby, "Quantum Dots Meet Biomolecules", C&E News, 8, (Sep. 28, 1988).

Kortan et al., "Nucleation and Growth of CdSe on ZnS Quantum Crystallite Seeds, and Vice Versa, in Inverse Micelle Media", J. Am. Chem. Soc., vol. 112, No. 4, pp. 1327–1332, (1990).

Lee et al. "Surface Derivatization of Nanocrystalline CdSe Semiconductors", Mat. Res. Soc. Symp. Proc., vol. 452, pp. 323–328 (1997).

Lett, D. N., "Color–Coding Quantum Dots Debut With Promising Careers In Clinical Diagnostics Field", BioWorld Today, vol. 9, No. 185, p. 1, (1998).

Mahtab et al., "Protein–Sized Quantum Dot Luminescence Can Distinguish Between "Straight", "Bent", And "Kinked" Oligonucleotides", J. Am. Chem. Soc., vol. 117, No. 35, pp. 9099–9100, (1995).

Mahtab et al., "Preferential Adsorption of a "Kinked" DNA to a Neutral Curved Surface: Comparisons to and Implications for Nonspecific DNA—Protein Interactions", J. Am. Chem. Soc., vol. 118, No. 30, pp. 7028–7032, (1996).

Mattoussi et al., " Self–assembly of CdSe—ZnSQuantum Dot Bioconjugates Using an Engineered Recombinant Protein", J. Am. Chem. Soc., vol. 122, No. 49, pp. 12142–12150, (2000).

Mattoussi et al., "Bioconjugation of Highly Luminescent Colloidal CdSe—ZnS Quantum Dots with an Engineered Two–Domain Recombinant Protein", phys. stat. sol. (b), vol. 224, No. 1, pp. 277–283, (2001).

McGall et al., "Light–directed synthesis of high–density oligonecleotide arrays using semiconductor photoresists", Proc. Natl. Acad. Sci., vol. 93, pp. 13555–13560, (1996).

Mikulec et al., "Fluorescent Semiconductor Nanocrystallites Derivatized With Biomolecules", Am. Chem. Soc. Abstracts of Papers Part 3, 018, (1998).

Murphy et al., "Quantum Dots as Inorganic DNA–Binding Proteins", Mat. Res. Soc. Symp. Proc., vol. 452, pp. 597–600, (1997).

Murray et al., "Synthesis and Characterization of Nearly Monodisperse CdE (E=S, Se, Te) Semiconductor Nanocrystallites", J. Am. Chem. Soc., vol. 115, No. 19, pp. 8706–8715, (1993).

Nozik et al., "Colloidal Quantum Dots Of III–V Semiconductors", MRS Bulletin, vol. 23, No. 2, pp. 24–30, (1998).

Schröck et al., "Multicolor Spectral Karyotyping of Human Chromosomes", Science, vol. 273, pp. 494–497, (1996).

Service, R. F., "Semiconductor Beacons Light Up Cell Structure", Science, vol. 281, pp. 1930–1931, (1998).

Wade, Nicholas, "In the Hunt for Useful Genes, a Lot Depends on 'Snips' ", New York Times, Section C, pp. 1 & 5, (1998).

Zhang et al., "Novel Flow Cytometry Compensation Standards: Internally Stained Fluorescent Microspheres With Matched Emission Spectra and Long–Term Stability", Cytometry, vol. 33, No. 2, pp. 244–248, (1998).

* cited by examiner

TCA GCT CAG TTG AAA AAA AAA TTG CAA GCA CTG AAG AAA AAG AAC GCT CAG CTG AAG
Ser Ala Gln Leu Lys Lys Lys Leu Gln Ala Leu Lys Lys Lys Asn Ala Gln Leu Lys

TGG AAA CTT CAA GCC GTC AAG AAG AAA CTC GCC CAG GGT GGG GAT TCA TGA-COOH
Trp Lys Leu Gln Ala Leu Lys Lys Lys Leu Ala Gln Gly Gly Asp Ser ***  ← STOP CODON ized moiety with such properties. In this instance, the macromolecule portion electrostatically self-assembles with the inorganic particle and the biological moiety interacts with a predetermined chemical species or biological target. As a result, the macromolecules forming the self-assembled supramolecular structures can be preselected so that the ionic conjugate will include a macromolecule that will directly or indirectly react with or exhibit affinity for a specific species.

INORGANIC PARTICLE CONJUGATES

CLAIM OF PRIORITY

This application claims priority to U.S. patent application Ser. No. 60/190,766 filed on Mar. 20, 2000, the entire contents of which are hereby incorporated by reference.

FEDERALLY SPONSORED RESEARCH OR DEVELOPMENT

This invention was made with government support under Contract No. DMR-98-08941 from the National Science Foundation and Contract Nos. N0001499WX30470 and N0001400WX20094 from the Office of Naval Research. The government may have certain rights in the invention.

BACKGROUND

This invention relates to ionic conjugates including inorganic particles and macromolecules, and more particularly to an electrostatic conjugate useful in detecting the presence or absence of specific species, such as for detecting a biological target.

Labeling of biological molecules using fluorescent tags is a common and useful practice in biological science. Fluorescent small molecules (conventional organic dyes) are used in both single and simultaneous multiple detection approaches. However, biological tagging using organic fluorophores has significant limitations. Fluorescent molecules tend to have narrow absorption spectra and their emission spectra are usually broad and exhibit red tailing, making simultaneous quantitative evaluation of relative amounts of different probes present in the same sample difficult due to spectral cross talk between various detection channels. Furthermore, any desired variations of the absorption and/or emission spectra of tagged bioconjugates require the use of distinct molecular labels with attendant synthesis and bioconjugation challenges. Nonetheless, the use of multiple labels has achieved a considerable level of sophistication, as demonstrated by recent flow cytometry work involving a three-laser system and eight-color marking scheme to simultaneously measure a total of 10 parameters on cellular antigens.

SUMMARY

An ionic conjugate forms through self-assembly in which inorganic particles electrostatically attach associate with at least one macromolecule. One type of association is self-assembly. Self-assembly is a coordinated action of independent entities under distributed (i.e., non-central) control to produce a larger structure or to achieve a desired group effect. Instances of self-assembly occur in biology, e.g., embryology and morphogenesis, and in chemistry, e.g., the formation of more loosely bound supramolecular structures from groups of molecules. Self-assembly of ionic conjugates is driven by noncovalent binding such as electrostatic interactions between charged, ionizable, or chargeable linking groups of the inorganic particles and complementary groups of the macromolecule.

Each of the macromolecules can also include a moiety that reacts with or exhibits an affinity for a predetermined chemical species or biological target. For example, the macromolecule can include an antibody, polynucleotide, or cell membrane having a charged, ionizable, or chargeable linking group. Alternatively, a macromolecule that does not react with or exhibit an affinity for a predetermined chemical species or biological target can be attached to a biological Inorganic particles such as semiconductor nanocrystals provide a solution to many of the problems encountered by organic small molecules in fluorescent tagging applications, by offering advantages such as a high photo-bleaching threshold, excellent chemical stability, and readily tunable spectral properties. Combining the size-dependent luminescence emission properties of the nanocrystals, their wide range of useful excitation and emission wavelengths, resistance to photo-bleaching, and a high quantum yield in aqueous solutions (high sensitivity) makes these materials very attractive for the labeling of biological targets via a self-assembled nanocrystal-macromolecule in which the macromolecule contains a moiety having an affinity for a specific biological target.

In one aspect, the invention features a composition including an inorganic particle, a linking group which has a distal end and a proximal end, the distal end being bound to an outer surface of the inorganic particle and the proximal end including a first charged or ionizable moiety, and a macromolecule having a second charged or ionizable moiety, in which the first and second charged or ionizable moieties associates the inorganic particle electrostatically with the macromolecule to form an ionic conjugate. The macromolecule can be a fusion protein having a second charged or ionizable moiety, wherein the first and second charged or ionizable moieties electrostatically associates the inorganic particle with the fusion protein to form an ionic conjugate.

In another aspect, the invention features a method of forming an ionic conjugate by providing an inorganic particle including a linking group having a distal end and a proximal end, the distal end being bound to an outer surface of the inorganic particle and the proximal end including a first charged or ionizable moiety; and contacting a macromolecule having a second charged or ionizable moiety with the inorganic particle, in which the first and second charged or ionizable moieties electrostatically associate the inorganic particle with the macromolecule to form an ionic conjugate. The method can further include contacting a plurality of macromolecules, each of the macromolecules including a charged or ionizable moiety, with the inorganic particle to electrostatically associate the plurality of macromolecules with the inorganic particle via a plurality of inorganic particle linking groups. The macromolecule can be formed by recombinant or synthetic methods, or isolated from a natural source. Each member of the plurality of macromolecules can be the same or different species.

In another aspect, the invention features, a method of detecting the presence of a predetermined species in a solution. The method includes contacting a solution with an ionic conjugate, in which the ionic conjugate includes an inorganic particle electrostatically associated with a macromolecule, the macromolecule capable of binding specifically to the predetermined species. The method can further includes forming an ionic conjugate by adding an inorganic particle and a macromolecule to the solution. The inorganic particle includes a linking group having a distal end and a proximal end, the distal end being bound to an outer surface of the inorganic particle and the proximal end including a first charged or ionizable moiety. The macromolecule includes a second charged or ionizable moiety. The first and second charged or ionizable moieties associate electrostatically to form the ionic conjugate.

Embodiments of the invention may include one or more of the following. The inorganic particle can be a semiconducting nanocrystal (QD). The semiconductor nanocrystal can include a first semiconductor material selected from the group consisting of a Group II-VI compound, a Group II-V compound, a Group III-VI compound, a Group III-V compound, a Group IV-VI compound, a Group I-III-VI compound, a Group II-IV-VI compound, and a Group II-IV-V compound. The first semiconductor material can be selected from the group consisting of ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, and mixtures thereof. The first semiconductor material can be CdSe. The first semiconductor material can be overcoated with a second semiconductor material. The second semiconductor material can be ZnS, ZnO, ZnSe, ZnTe, CdS, CdO, CdSe, CdTe, MgS, MgSe, HgO, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, $SiO_2$, or mixtures thereof.

The inorganic particle can include a plurality of linking groups each independently including a charged or ionizable moiety. The ionic conjugate can include a plurality of macromolecules, each of the macromolecules including a charged or ionizable moiety. The plurality of macromolecules can associate with the inorganic particle via electrostatic interaction with the plurality of inorganic particle linking groups. The inorganic particle can include Ag, Au, or a phosphor. The first and second charged or ionizable groups can include hydroxide, alkoxide, carboxylate, sulfonate, phosphate, phosphonate, or quaternary ammonium. The second charged or ionizable moiety can be a leucine zipper. The second charged or ionizable moiety can be polyaspartate. The macromolecule can include a polypeptide or polynucleotide, such as a maltose binding protein or an immunoglobulin G binding protein.

The linking group can have the formula:

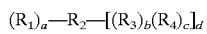

wherein $R^1$ is selected from the group consisting of C1–C100 heteroalkyl, C2–C 100 heteroalkenyl, heteroalkynyl, —OR, —SH, —NHR, —NR'R", —N(O)HR, —N(O)R'R", —PHR, —PR'R", —P(NR'R")NR'R", —P(O)R'R", —P(O)(NR'R")NR'R", —P(O)(OR')OR", —P(O)OR, —P(O)NR'R", —P(S)(OR')OR", and —P(S)OR, wherein R, R', R" are independently selected from the group consisting of H, a branched or unbranched C1–C100 alkyl, a branched or unbranched C2–C100 alkenyl, a branched or unbranched C2–C100 alkynyl, a branched or unbranched C1–C100 heteroalkyl, a branched or unbranched C2–C100 heteroalkenyl, a branched or unbranched C2–C100 heteroalkynyl, with the proviso that when a is greater than 1 the $R_1$ groups can be attached to the $R_2$ or $R_3$ groups at the same or different atoms within those groups, the $R_1$ groups can be the same or different, or the $R_1$ groups can form a six, seven, eight, nine, or ten membered cycloalkyl, cycloalkenyl, heterocyclic, aryl, heteroaryl, or a six- to thirty-membered crown ether or heterocrown ether;

$R_2$ is selected from a bond, a branched or unbranched C2–C 100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_3$ is selected from a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteoaryl;

$R_4$ is selected from the group consisting of hydrogen, a carboxylate, a thiocarboxylate, an amide, a hydrazine, a sulfonate, a sulfoxide, a sulfone, a sulfite, a phosphate, a phosphonate, a phosphonium ion, an alcohol, a thiol, an amine, an ammonium, an alkyl ammonium, a nitrate; and a is 1 to 40, b is 0 to 3, c is 1 to 30, d is 1 to 3, and when d is 2 or 3 the $R_3$ groups can be the same or different or can be linked together to form a five to ten members cycloalkyl, cycloalkenyl, heterocyclic, aryl, or heteroaryl. The linking group can have the formula $HS-C_2H_4-CH(SH)-(C_4H_8)-COOH$.

In another aspect, the invention features a method of forming an ionic conjugate from a modified inorganic particle and a macromolecule. Both the particle and molecule include charged or ionizable linking groups which together can form complimentary ionic pairs to electrostatically attach at least one macromolecule to the particle. The inorganic particle can be modified by bonding one charged or ionizable linking group to the particle surface. The macromolecule can be a modified protein, such as by a recombinant protein process, to incorporate one end of a charged or ionizable linking group, such as a chargeable polypeptide, onto the protein's surface.

In another aspect, the invention features, a recombinant protein electrostatically attached to a semiconducting nanoparticle. The recombinant protein can be a fusion protein including any protein imparting biological activity which has been modified, for example, to include a basic leucine zipper. The leucine zipper is a chargeable polypeptide having one end bound to the protein and another end unbound and protruding away from the surface of protein. The zipper also includes a thiol group which can form a covalent bond with the thiol group of a leucine zipper of another fusion protein to form a dimer of fusion proteins. The semiconducting nanoparticle can include dihydrolipoic acid groups which electrostatically interact with the unbound end of the basic leucine zipper to form the ionic conjugate.

In another aspect, the invention features a nanoparticle having a core and overcoat. During routine preparation, an inorganic core of the nanocrystal is capped with an organic shell such as a trioctyl phosphine and trioctyl phosphine oxide mixture (TOP/TOPO), which can be further modified and thereby, permit post synthesis manipulation and tailoring of particle solubility in various solvents. Overcoating the CdSe core, for example, with a larger band gap semiconducting material, e.g., ZnS or CdS, a process based on the concepts of band-gap engineering used in electronics, permits passivation of core surface states and reduces the leakage of excitons outside the core. This overcoating enhances the photochemical stability of these materials and improves the luminescence quantum yield substantially without affecting the wavelength and the spectral width of the emission, i.e., CdSe—ZnS nanoparticles have an FWHM~40–60 nm. In addition, overcoating can enhance resistance to photo-bleaching. The above properties enhance the sensitivity of detection approaches employing these nanoparticles for signal generation. Substantial PL intensities with good signal-to-noise ratios, along with well-resolved spectra, are measured for dispersions with concentrations much smaller than 1 nanomole of nanoparticles per liter. Replacing the TOP/TOPO cap with polar terminated groups allows dispersal of these core-overcoat nanoparticles in aqueous solutions with preservation of a high photoluminescence quantum yield. Presence of a dihydrolipoic acid provided stable water dispersions of CdSe—ZnS nanoparticles with quantum yields of 15–20%. The dihydrolipoic acid groups on the surface of the nanoparticles are charged or ionizable groups which electrostatically attach to complimentary charged or ionizable groups of a macromolecule.

The ionic conjugates of this invention exhibit biological activity, are chemically stabile, and exhibit increased quantum yield relative to inorganic particles lacking an electrostatically bound protein. The conjugates also unexpectedly exhibit reduced aggregation relative to biological conjugates in which a biological moiety is covalently bound directly to the inorganic particle. Another advantage of the process of producing ionic conjugates of this invention is its simplicity and versatility. For example, the desired protein attaches to the surface of the inorganic particle nearly instantaneously.

Ionic conjugates including CdSe nanocrystals overcoated with ZnS and dithiol capping groups and self-assembled with macromolecules offer several advantages: 1) because each dithiol-capping molecule can attach to two surface atoms, a higher surface passivation can be achieved with equal or even smaller density of capping groups per unit area, in comparison with mono-thiol capping molecules, for instance. 2) The carboxylic acid groups, which permit dispersion of the nanocrystals in water solutions at basic pH, also provides a surface charge distribution that can be used to directly self-assemble (or react) with other macromolecules having a net positive charge. 3) The ZnS coverage provides a better shielding of the CdSe core from the polar environment and a more efficient confinement of the exciton (electron-hole pair), which results in stable and highly luminescent nanocrystal dispersions in water. Dispersions of core-overcoat nanocrystals in water that are stable over a long period of time (several months) and a photoluminescence quantum yield of ~20% are easily prepared using the above approach. 4) The synthetic approach can be easily applied to a number of different core-overcoat nanocrystals and extended to other combinations of semiconducting materials, II-VI and III-V, which can generate a group of fluorescent probes that can be spectrally tuned. This contrasts with the need of developing specific chemistry routes for each organic fluorescent dye case-by-case. 5) The synthesis of a macromolecule such as fusion proteins based on the construction vector strategy provides a general and consistent scheme to prepare a wide selection of biological macromolecules that can perform specific functions and self-assemble with the nanocrystals. 6) The recombinant protein approach permits one to perform alterations of charged or ionizable portion of the macromolecule, e.g., charge, size, stability to pH and temperature, and thereby allow one to vary and control the self-assembly of the macromolecule such as to form monomers, dimers and tetramers of macromolecules which can self-assemble onto the inorganic particle. Each of the macromolecules can include moieties having affinities for the same or different biological agents. 7) Controlling the properties of the peptide tail permits these proteins to interact non-covalently with a variety of materials (e.g., inorganic colloidal particles and even surfaces) that have opposite charge to those on the linker tail of the proteins.

The details of one or more embodiments of the invention are set forth in the accompanying drawings and the description below. Other features, objects, and advantages of the invention will be apparent from the description and drawings, and from the claims.

DETAILED DESCRIPTION

The ionic conjugates include an inorganic particle electrostatically associated with a macromolecule. The macromolecule can be selected to interact with a predetermined species. As a result, the ionic conjugates can be used in assays to detect the presence of or to quantify the amounts of specific compounds, detect specific interactions of biological systems, detect specific biological processes, detect alterations in specific biological processes, or detect alterations in the structure of specific compounds.

Figure 1:
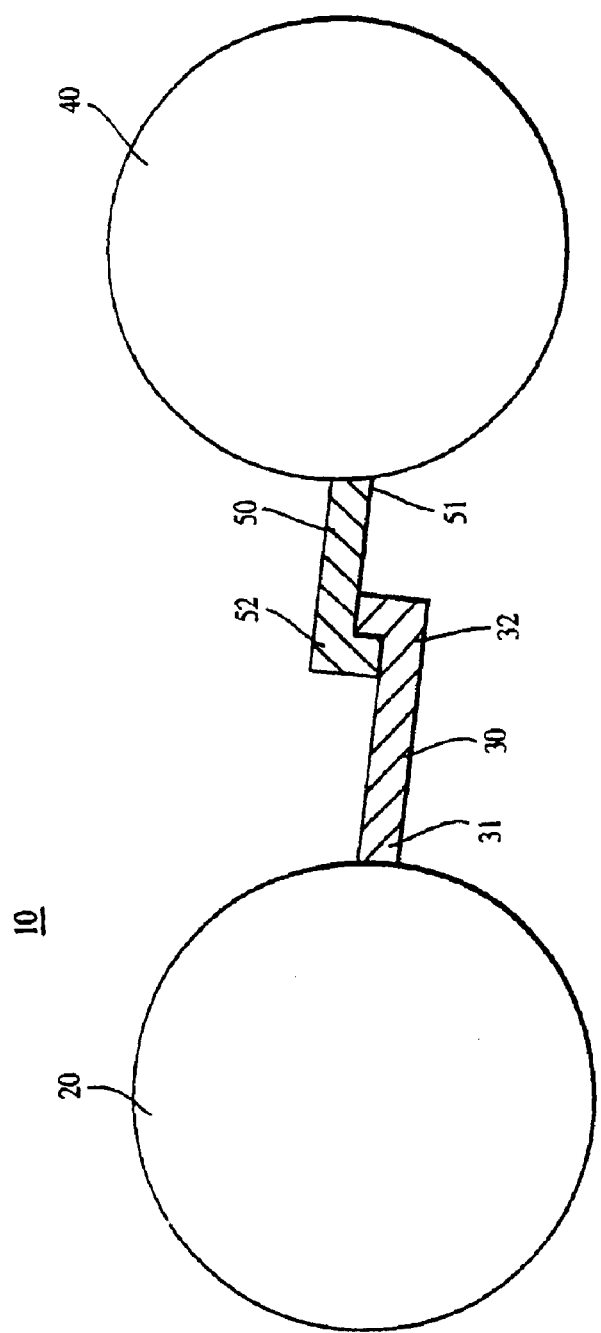
FIG. 1 is a schematic view of an ionic conjugate of this invention.

Referring to FIG. 1, an ionic conjugate 10 includes an inorganic particle 20 and a macromolecule 40 each of which include a linking group 30 and 50, respectively, to associatively bind particle 20 to macromolecule 40 at ends 31 and 51. Ends 31 and 51 are charged or ionizable, i.e., the ends can contain localized amounts of positive or negative charge, and form complementary ionic or electrostatic pairs, such as a partial negative charge on end 31 and a partial positive on charge 51, or vice versa. In general, macromolecule 40 includes a linking group at any location in or on the macromolecule that is accessible to interact electrostatically with linking group 30 to attach the macromolecule to inorganic particle 20. Typically, the charged or ionizable portion of linking group 50 extends (protrudes) away from the macromolecule 40.

In general the inorganic particle can be any inorganic material exhibiting a distinct physical property that can be used to identify that material. The physical properties can be, but are not limited to, magnetic properties or optical properties. Optical properties include, but are not limited to, emission such as photoluminescence, absorption, scattering and plasmon resonances. For example, the inorganic particle can be illuminated with a light source at an absorption wavelength to cause an emission at an emission wavelength that can be used to distinguish the emitting material from other materials.

Examples of inorganic particles include, but are not limited to, inorganic colloids and semiconducting nanoparticles. The particles can be metallic or magnetic particles. The particles also can be crystalline particles. Examples of inorganic colloids include Ag, Au, or a phosphor. The phosphor can be a inorganic phosphor, such as a rare earth oxide. The inorganic colloids can exhibit distinct reflectivity and scattering properties, plasmon resonances, to radiation depending on the size of the particles in the colloid. Examples of semiconducting nanoparticles include, but are not limited to, elements from groups II-VI, III-V, and IV of the periodic table. Elements from these groups include, but are not limited to, CdS, CdSe, CdTe, ZnS, ZnSe, ZnTe, MgTe, GaAs, GaP, GaSb, GaN, HgS, HgSe, HgTe, InAs, InP, InSb, InN, AlAs, AlP, AlSb, AlS, PbS, PbSe, Ge, Si, or an alloy or mixture thereof, including ternary and quaternary mixtures. The semiconducting nanoparticles can be semiconducting nanocrystals. The nanocrystals can be illuminated with a light source at an absorption wavelength to cause an emission at an emission wavelength. The emission has a frequency that corresponds to the band gap of the quantum confined semiconductor material. The band gap is a function of the size of the nanocrystal. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region. The narrow size distribution of a population of nanocrystals can result in emission of light in a narrow spectral range. The population can be monodisperse and can exhibit less than a 15% rms deviation in diameter of the nanocrystals, preferably less than 10%, more preferably less than 5%. Spectral emissions in a narrow range of no greater than about 75 nm, preferably 60 nm, more preferably 40 nm, and most preferably 30 nm full width at half max (FWHM) can be observed. The breadth of the emission decreases as the polydispersity of nanocrystal diameters decreases. Semiconductor nanocrystals can have high emission quantum efficiencies such as greater than 10%, 20%, 30%, 40%, 50%, 60%, 70%, or 80%.

The semiconductor forming the nanocrystals can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, Alp, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

Methods of preparing monodisperse semiconductor nanocrystals include pyrolysis of organometallic reagents, such as dimethyl cadmium, injected into a hot, coordinating solvent. This permits discrete nucleation and results in the controlled growth of macroscopic quantities of nanocrystals. Preparation and manipulation of nanocrystals are described, for example, in U.S. application Ser. No. 08/969,302, incorporated herein by reference in its entirety. The method of manufacturing a nanocrystal is a colloidal growth process. Colloidal growth occurs by rapidly injecting an M donor and an X donor into a hot coordinating solvent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M donor or X donor, the growth period can be shortened.

The M donor can be an inorganic compound, an organometallic compound, or elemental metal. M is cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis (silyl) chalcogenide, dioxygen, an ammonium salt, or a tris(silyl) pnictide. Suitable X donors include dioxygen, bis(trimethylsilyl) selenide ($(TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ($(TMS)_2Te$), bis (trimethylsilyl)sulfide ($(TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl) phosphide ($(TMS)_3P$), tris(trimethylsilyl) arsenide ($(TMS)_3As$), or tris(trimethylsilyl) antimonide ($(TMS)_3Sb$). In certain embodiments, the M donor and the X donor can be moieties within the same molecule.

A coordinating solvent can help control the growth of the nanocrystal. The coordinating solvent is a compound having a donor lone pair that, for example, has a lone electron pair available to coordinate to a surface of the growing nanocrystal. Solvent coordination can stabilize the growing nanocrystal. Typical coordinating solvents include alkyl phosphines, alkyl phosphine oxides, alkyl phosphonic acids, or alkyl phosphinic acids, however, other coordinating solvents, such as pyridines, furans, and amines may also be suitable for the nanocrystal production. Examples of suitable coordinating solvents include pyridine, tri-n-octyl phosphine (TOP) and tri-n-octyl phosphine oxide (TOPO). Technical grade TOPO can be used.

Size distribution during the growth stage of the reaction can be estimated by monitoring the absorption line widths of the particles. Modification of the reaction temperature in response to changes in the absorption spectrum or emission spectrum of the particles allows the maintenance of a sharp particle size distribution during growth. Reactants can be added to the nucleation solution during crystal growth to grow larger crystals. By stopping growth at a particular nanocrystal average diameter and choosing the proper composition of the semiconducting material, the emission spectra of the nanocrystals can be tuned continuously over the wavelength range of 400 nm to 800 nm. The nanocrystal has a diameter of less than 150 Å. A population of nanocrystals has average diameters in the range of 15 Å to 125 Å.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The core can have an overcoating on a surface of the core. The overcoating can be a semiconductor material having a composition different from the composition of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnO, ZnSe, ZnTe, CdS, CdO, CdSe, CdTe, MgS, MgSe, HgO, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, $SiO_2$, or mixtures thereof. For example, ZnS, ZnSe or CdS overcoatings can be grown on CdSe or CdTe nanocrystals. An overcoating process is described, for example, in U.S. application Ser. No. 08/969,302, incorporated herein by reference in its entirety. By adjusting the temperature of the reaction mixture during overcoating and monitoring the absorption spectrum or absorption spectrum of the core, over coated materials having high emission quantum efficiencies and narrow size distributions can be obtained.

The particle size distribution can be further refined by size selective precipitation with a poor solvent for the nanocrystals, such as methanol/butanol as described in U.S. application Ser. No. 08/969,302, incorporated herein by reference. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

The outer surface of the nanocrystal can include a layer of compounds derived from the coordinating solvent used during the growth process. The surface can be modified by repeated exposure to an excess of a competing coordinating group to form an overlayer. For example, a dispersion of the capped nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Transmission electron microscopy (TEM) or small angle x-ray scattering (SAXS) can provide information about the size, shape, and distribution of the nanocrystal population. Powder x-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from x-ray diffraction data using, for example, the Scherrer equation. It also can be estimated from the UV/Vis absorption spectrum.

A macromolecule can be any, organic or inorganic, species including a charged, chargeable, or ionizable group. The charged, chargeable, or ionizable group can be, but is not limited to, a carboxylate, a thiocarboxylate, an amide, a hydrazine, a sulfonate, a sulfoxide, a sulfone, a sulfite, a phosphate, a phosphonate, a phosphonium ion, an alcohol, a thiol, an amine, an ammonium, a quarternary ammonium, an alkyl ammonium, or a nitrate. For example, the ionizable group can be an acidic or basic side chain of an amino acid such as lysine, arginine, histidine, aspartate, or glutamate. The macromolecule can include a plurality of ionizable groups such in polylysine, poly (acrylic acid) (PAA), poly (allyl amine hydrochloride) (PAH), sulfonated polystyrene (SPS), and polydiallyldimethylammonium chloride (PDADMAC). The macromolecule can be a polypeptide or a polynucleotide.

The macromolecule can exhibit a specific interaction with a separate molecule or biological target. For example, the macromolecule can include a protein, antibody, DNA, RNA, or cell membrane, which binds, interacts, or complexes with a specific compound. Alternatively, a macromolecule that does not exhibit a desired affinity for a predetermined species can be attached to a chemical or biological moiety, such as a protein, antibody, DNA, RNA, or cell membrane, that exhibits the desired interaction. For example, the macromolecule can be attached to the chemical or biological moiety by biological processes, e.g., from cultures of recombinant organisms (bacteria, yeast, insect, or mammalian cells), or, alternatively, by totally synthetic or semi-synthetic methods. The biological moiety, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to bacterial cells, e.g., mammalian, yeast, insect or plant cell expression systems. Examples of biological moieties include maltose binding protein (MBP) and immunoglobulin G binding protein (Protein G).

Alternatively, nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, subcloning, labeling probes, sequencing, hybridization and the like are well described in the scientific and patent literature, see, e.g., Sambrook, ed., Molecular Cloning: a Laboratory Manual (2nd ed.), Vols. 1–3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993). Techniques for inserting a charged or ionizable macromolecule, such as leucine zippers, are also discussed in "Peptide 'Velcro': Design of a Heterodimeric Coiled Coil," Current Biology 3(10), 658–667 (1993), by O'Shea et al. and in "Fiber-Optic Fluorometric Sensing of Polymerase Chain Reaction-Amplified DNA Using an Immobilized DNA Capture Protein," Analyt. Biochemistry 235, 61–72 (1996), by Mauro et al.

Recombinant (fusion) proteins can be prepared in a constructed plasmid (double stranded DNA) using appropriate cloning strategies, a technique familiar in bioengineering manipulation of molecules. The cloning and the protein expression steps can be carried out in *Escherichia coli* (*E. coli*), which also serves as the growth environment. Appropriate and specific enzymes (restriction endonucleases) can be introduced to cut the plasmid at the proper polylinker cloning site where the gene with the specific function is introduced. A linking group such as a peptide tail can then be cloned on the carboxy terminal end of the coding region of the biological moieties having a desired function. Biological moieties include the maltose binding protein (MBP), which binds to the sugar maltose with high affinity, and protein G, which is known to specifically bind, through its b-subunit, to the Fc region of immoglobulin G (IgG). The biological moieties also can be further mutated such that the moieties exhibits a desired function, such as binding to a specific biological target. For instance, protein G can be modified both to interact with a specific molecule and to incorporate a leucine zipper functionality. Protein G then can be electrostatically attached to the inorganic particle and used to detect interactions with the specified biological target.

A synthetic method for attaching the macromolecule to a biological moiety can be performed via known solid-phase peptide coupling technology. For example the macromolecule can be formed of a single covalently-linked polypeptide chain including an charged or ionizable portion and a portion exhibiting biological specificity. Synthetic methods for producing the macromolecule can include processes in which all or part of either or both constituent polypeptides, i.e., the charged or ionizable and biologically specific portions, forming the macromolecule are prepared using in vitro synthesis. Alternatively, all or part of either or both constituent polypeptide chains can be prepared using the above recombinant organism(s). For example, the charged or ionizable portion of a polypeptide can be produced synthetically and the biologically specific portion can be obtained by recombinant or synthetic methods. If the charged/ionizable and biologically specific portions are obtained independently, they can be attached by a) a chemical means after chemically activating the peptide termini, such as with EDC (1-ethyl-3,3-dimethylaminopropyl carbiimide) coupling, b) enzymatically assisted catalysis of activated or unactivated polypeptides, c) formation of disulfide (S—S) bonds promoted by oxidation utilizing $O_2$ or by additional chemical or enzymatic means, or d) by utilizing non-covalent electrostatic or hydrophobic interactions separate from the self-assembly interactions used to electrostatically attach a macromolecule to a particle. The synthetic methods also include attaching charged or ionizable portions by any of the above methods to polynucleic acid aptamers (DNA or RNA), peptide nucleic acid (PNA) oligomer, oligosaccharides, lipopolysaccharide, polydextrins, cyclic polydextrins, crown ethers or similar derivatives, and other natural or synthetic "receptor" species.

In alternative synthetic approach, a self-assembled complex can be formed via an electrostatic conjugation of a positively charged polyelectrolyte, such as polydiallydimethlyammonium chloride, with a negatively charged phosphine-carboxylic acid complex, such as tris 2-carboxyethylphophine. The resulting complex can be coupled to the particles, with the phosphine groups providing a tether to bind to the particle surface, while the positively charged polymer facilitates particle water-soluble. The charged polymers can include terminal amine or hydroxyl groups, or can be copolymerized with an amino or hydroxyl group containing monomer, such as allyl amine and hydroxymethacrylate. Standard EDC-type coupling chemistry can be used to effectuate a linkage, such as via a peptide bond, between the amino or hydroxyl groups and a biological moiety to produce a self-assembled ionic conjugate that exhibits an specific biological affinity.

Figure 2A:
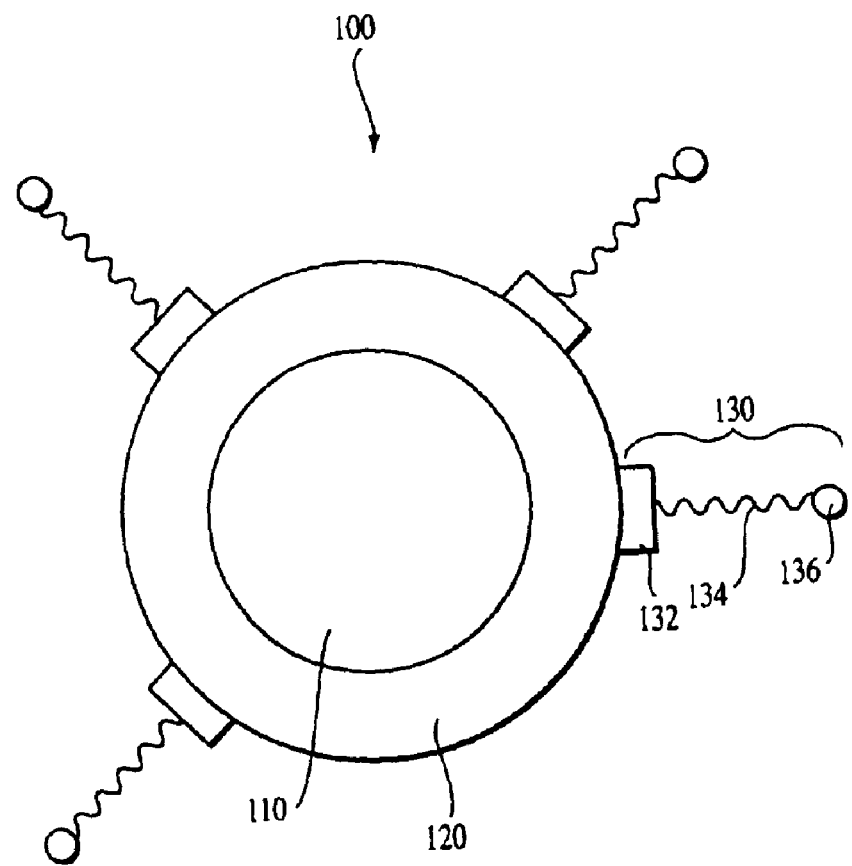
FIGS. 2A–2B are schematic cross-sections of inorganic particles of the ionic conjugates of FIG. 1.

Referring to FIG. 2A, in some embodiments, the inorganic particle is a semiconducting nanocrystal 100 including a semiconducting core 110 and a overcoat 120 encapsulating the core. Semiconducting core 110 and overcoat 120 are made of the semiconducting elements described above. A plurality of linking groups 130 attach to a surface of overcoat 120 via a surface interactive group 132 which associates with the materials of the overcoat or nanocrystal. Typically, the band gap energy of the overcoat material is larger than the band gap energy of the core. Each linking group 130 also contains a charged or ionizable group 136 tethered to surface interactive group 132 by a spacer 134. In general, spacer 134 is long enough to prohibit electron charge transfer between groups 132 or 120 and 136.

Figure 2B:
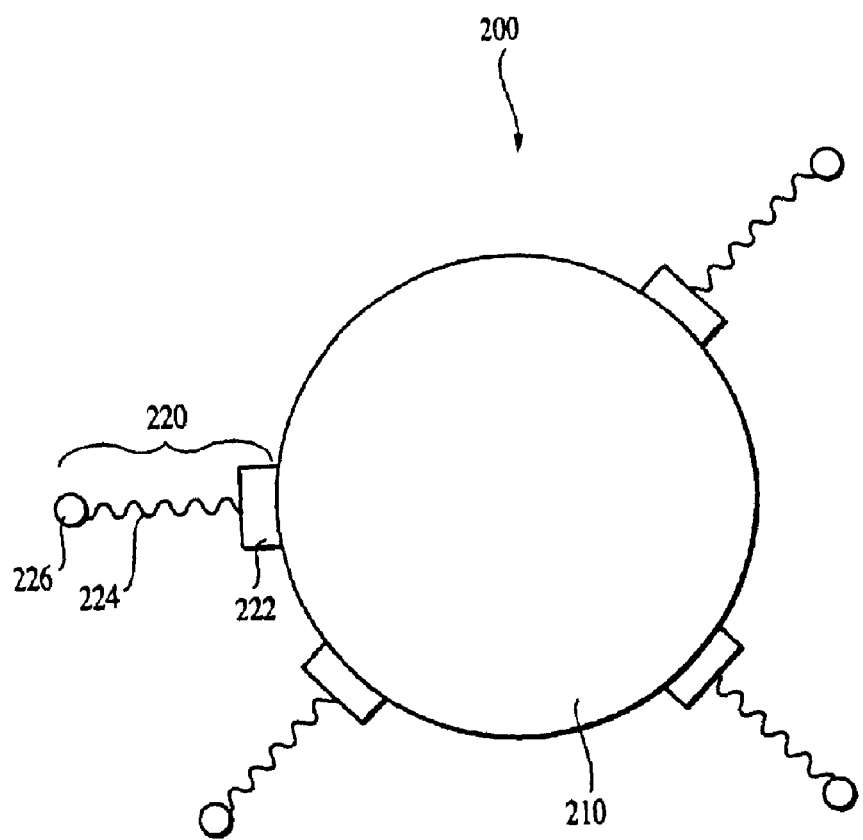

Referring to FIG. 2B, in other embodiments, an inorganic particle 200 of this invention is an inorganic colloid particle 210 having a plurality of linking groups 220 attached to a surface of particle 210 via a surface interactive group 222. Linking group 220 is similar to linking group 130 described above and includes a charged or ionizable group 226 and a spacer 224.

In general, the inorganic particles of this invention have a diameter between about 10 Å and about 1000 Å; preferably between about 10 Å and about 500 Å; and most preferably between about 10 Å and about 250 Å. The size dispersion about a mean size of the inorganic particles, typically, is less than about 20%; preferably less than about 15%; and more preferably less than about 10%; and most preferably less than about 5%. In general, more than about 40%; preferably more than about 50% fall; and most preferably more than about 60% of the particles fall within a specified particle size range.

The surface interactive group can be any chemical moiety having elements or chemical groups contained therein that are capable of binding to the surface of the inorganic particle. For example, the surface group can include S, N, P, O, or O=P groups. Charged or ionizable groups 136 and 226 can include any ionizable chemical group or any chemical group having a native charge, such as a quarternary ammonium group. Examples of charged or ionizable chemical groups include, but are not limited to, hydroxides, alkoxides, carboxylate, sulfonate, phosphate, phosphonate, quaternary ammonium, and the like.

Linking groups 30, 130, 220 also help to form a water-solubilizing layer around the particles. In certain embodiments, the surface of the inorganic particle includes a plurality of linking groups, some of which help to water-solubilize the particle and do not electrostatically associate with macromolecules, and others which do. The linking groups also can make the particles more stable (i.e., the particles can be used in dilute concentrations). For example, a monodentate linking group can be put on the surface of the particle, and then by self-assembly, a monolayer of an oligomer can be wrapped around the particle to effectively cross-link the functional groups on the surface of the particle. Self-assembly permits control of assembling the ionic conjugates at the nanometer scale and is similar to the technique of layer-by-layer self-assembly (or sequential adsorption) used to assemble large synthetic and biological polymers. See for example "Molecular-Level processing of Conjugated Polymers .1. Layer-by-Layer Manipulation of Conjugated Polyions," Macromolecules 28, 7107 (1995), by M. Ferreira and M. F. Rubner; "New Nanocomposite Films for Biosensors: Layer-by-Layer Adsorbed Films of Polyelectrolytes, Proteins or DNA," Biosensors & Bioelectronics 9, 677–684 (1994), by Decher et al.; and "Fuzzy Nanoassemblies: Toward Layered Polymeric Multicomposites," Science 277: 1232–1237 (1997), by G. Decher.

In preferred embodiments linking groups 30, 130, and 220 have the formula:

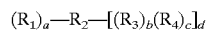

wherein $(R_1)_a$ is one or more surface interactive groups, $R_2$ is the spacer, and $[(R_3)_b(R_4)_c]_d$ is the charged or ionizable group;

$R_1$ is selected from the group consisting of C1–C100 heteroalkyl, C2–C100 heteroalkenyl, heteroalkynyl, —OR, —SH, —NHR, —NR'R", —N(O)HR, —N(O)R'R", —PHR, —PR'R", —P(NR'R")NR'R", P(O)R'R", P(O)(NR'R")NR'R", —P(O)(OR')OR", P(O)OR, P(O)NR'R", —P(S)(OR')OR", and P(S)OR, wherein R, R', R" are independently selected from the group consisting of H, a branched or unbranched C1–C100 alkyl, a branched or unbranched C2–C100 alkenyl, a branched or unbranched C2–C100 alkynyl, a branched or unbranched C1–C100 heteroalkyl, a branched or unbranched C2–C100 heteroalkenyl, a branched or unbranched C2–C100 heteroalkynyl, with the proviso that when a is greater than 1 the $R_1$ groups can be attached to the $R_2$ or $R_3$ groups at the same or different atoms within those groups, the $R_1$ groups can be the same or different, or the $R_1$ groups can form a six, seven, eight, nine, or ten membered cycloalkyl, cycloalkenyl, thereocyclic, aryl, heteroaryl, or a six- to thirty-membered crown ether or heterocrown ether;

$R_2$ is selected from a bond (i.e., $R_2$ is absent in which case $R_1$ attaches to $R_3$), a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_3$ is selected from a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_4$ is selected from the group consisting of hydrogen, a carboxylate, a thiocarboxylate, and amid, an amine, a hydrazine, a sulfonate, a sulfoxide, a sulfone, a sulfite, a phosphate, a phosphonate, a phosphonium ion, an alcohol, a thiol, an amine, an ammonium, an alkyl ammonium, a nitrate; and a is 1 to 4, b is 0 to 3, c is 1 to 3, d is 1 to 3, and when d is 2 or 3 the $R_3$ groups can be the same or different or can be linked together to form a five to ten members cycloalkyl, cycloalkenyl, heterocyclic, aryl, or heteroaryl.

In another preferred embodiment, the linking group 130 has the formula:

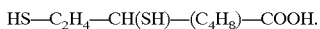

Methods for preparing inorganic particles such as semiconducting CdSe nanoparticles with or with a overcoat material are discussed, for example, in "Semiconductor Nanocrystal Colloids: Manganese Doped Cadmium Selenide, (Core)Shell Composites for Biological Labeling, and Highly Fluorescent Cadmium Telluride," MIT PhD Thesis, September 1999, by F. V. Mikulec, in "(CdSe)ZnS core-shell nanocrystals: Synthesis and characterization of a size series of highly luminescent nanocrystallites," J. Phys. Chem. B 101, 9463–9475 (1997), by Dabbousi et al.; and in "Semiconductor Nanocrystals as Fluorescent Biological Labels," Science 281, 2013–2016 (1998) by Bruchez, Jr., et al.

Figures 3A, 3B:
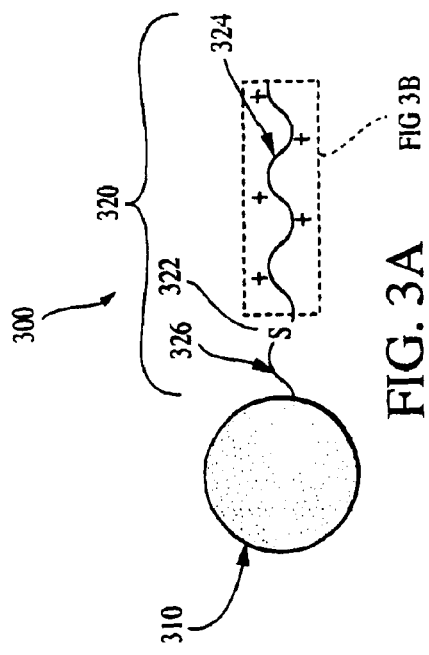
FIG. 3A is a schematic view of a recombinant protein, a fusion protein, of the ionic conjugates of FIG. 1.
FIG. 3B is diagrammatic view of an ionizable linking group protruding from the surface of the recombinant protein of FIG. 3A.
Figure 3C:
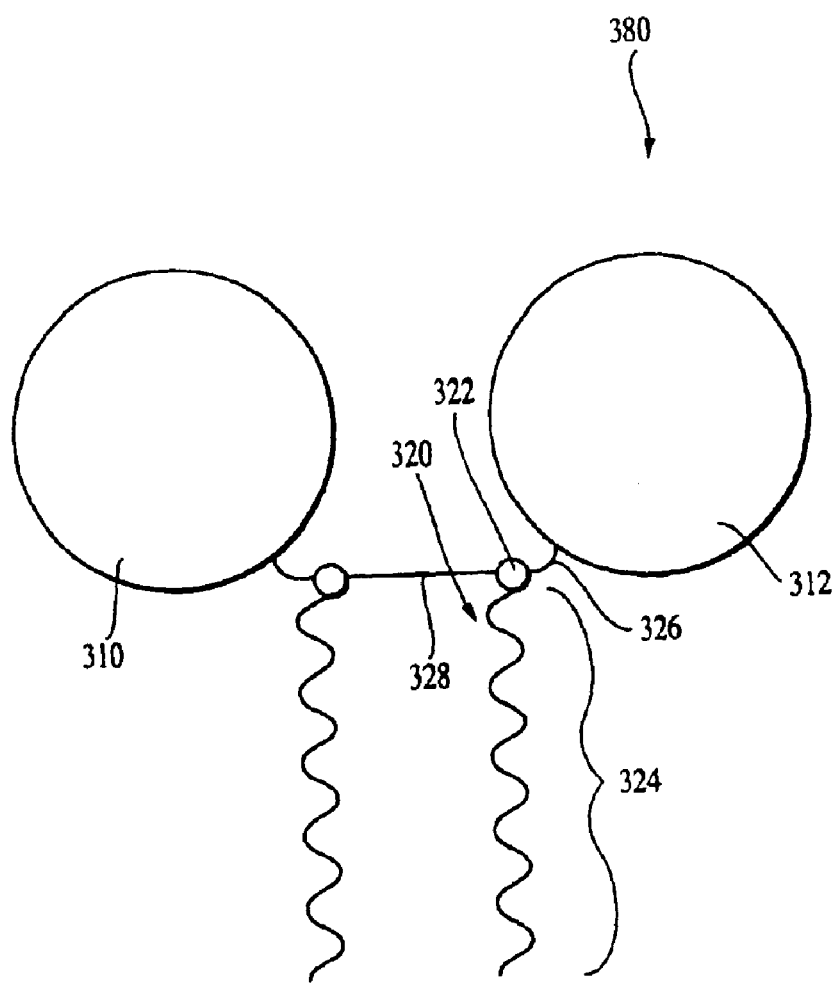
FIG. 3C is a schematic view of another recombinant protein of the ionic conjugate of FIG. 1.

Referring to FIGS. 3A–3C, a biological moiety 300, e.g., a recombinant protein having a specific biological function, includes protein 310 and a linking group 320 protruding from the surface of protein 310. Linking group 320 includes a coupling segment 326, such as a poly Asn linker, a bridging group 322, such as sulfur, and a tail 324. In certain embodiments, tail 324 is a polypeptide including approximately 30 amino acid residues. For example, tail can be any polypeptide which is charged or ionizable, i.e., contains localized amounts of positive or negative charge. FIG. 3B shows a positively charged tail 324 commonly referred to as a leucine zipper. Other possible tails include, but are not limited to, polypeptides including arginine or aspartate groups. Typically, proteins having a leucine zipper tend to form dimers to minimize hydrophobic interactions (FIG. 3C). The resulting dimers are a high probability state for proteins encoded with leucine. Dimer 380, shown in FIG. 3C, includes two separate proteins 310 and 312, which can be the same (a homodimer) or different (a heterodimer), linked via two bridging groups 322, e.g., thiol groups. Tails 324 are attached to the surface of each protein through coupling group 326 which can be an atom or a molecule, such as a polypeptide. Each of the bridging groups and coupling groups can be the same or different.

Figure 4A:
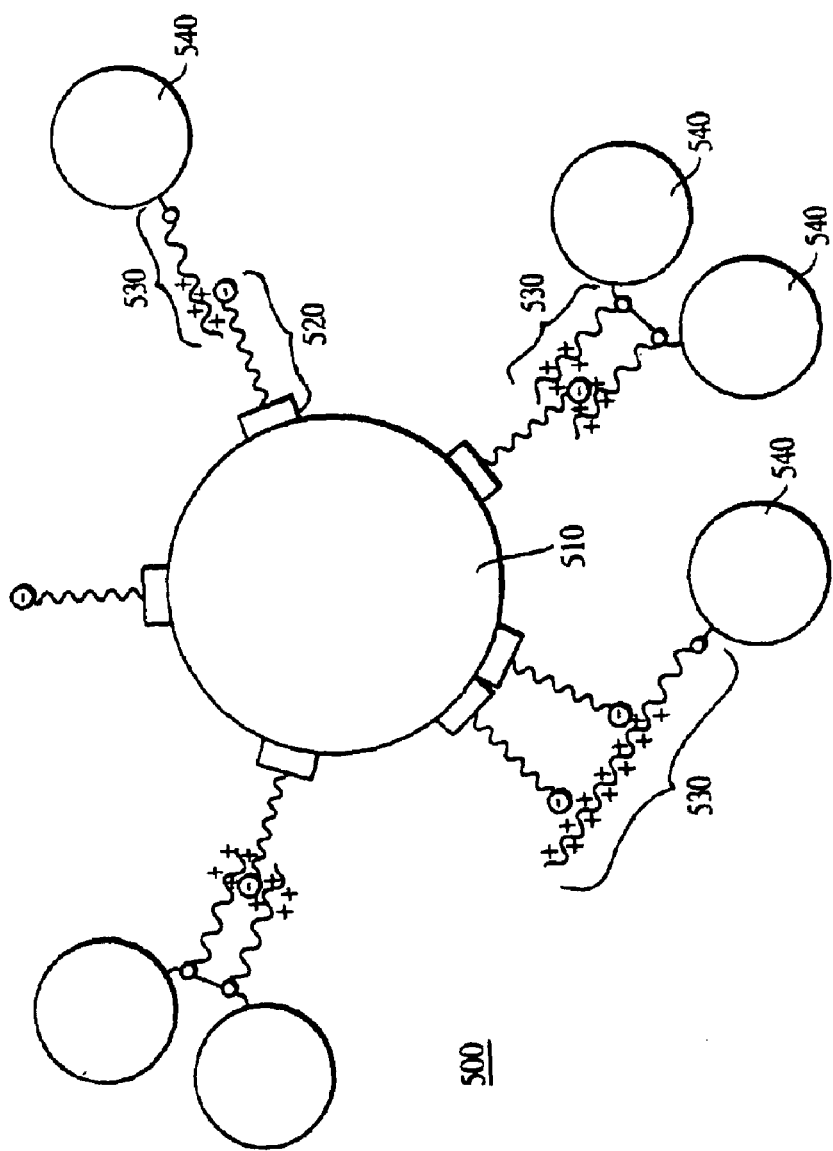
FIGS. 4A–4B are a detailed view of the ionic conjugate shown in FIG. 1.
Figure 4B:
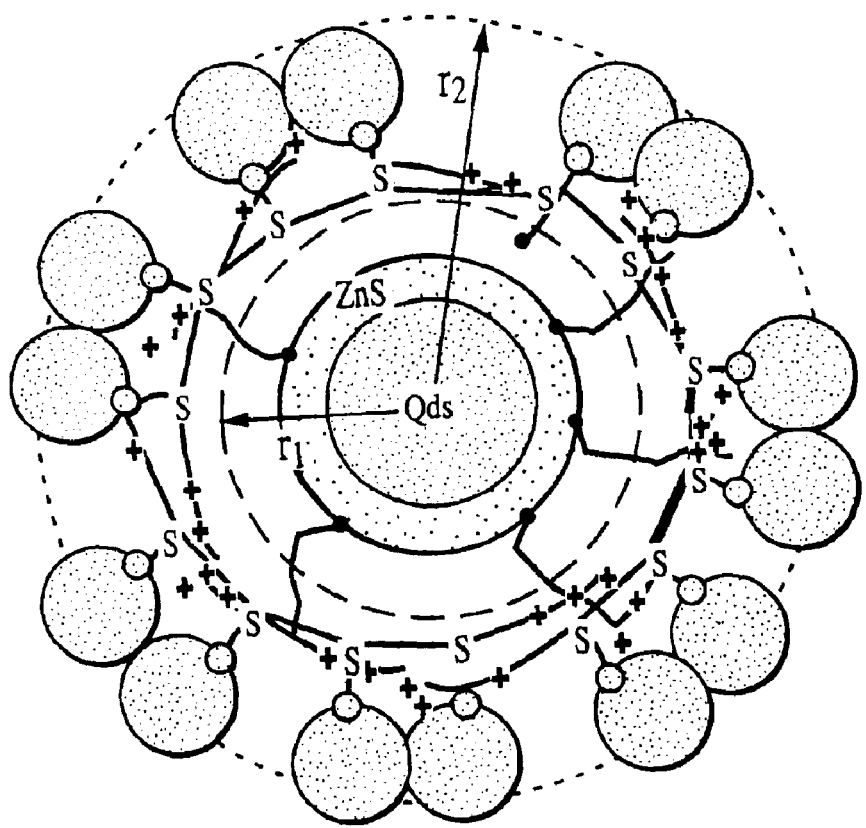

Referring to FIG. 4A, an ionic conjugate 500 includes an inorganic particle 510 electrostatically attached to proteins 540 via linking groups 520 and 530. In general, the biological moieties can electrostatically attach to the inorganic particle either as dimers or monomers. The dimer can be a homodimer or a heterodimer. Additionally, particle 510 can be electrostatically associated with several proteins which can be identical or different. A particle including different proteins can be used to simultaneously detect multiple biological targets of interest. Of course, the exact number of proteins attached to the particle depends on the diameter of the particle, the overall length of the linking groups, and the size of the protein. As seen in FIG. 4B, the number of proteins, N is given by the relationship:

$$N \propto (4\pi/3)(r_2^3-r_1^3)/V(\text{protein})$$

Where $r_2$ and $r_1$ are shown in FIG. 4B, $(r_2^3-r_1^3)$ is the volume of space available for protein packing and V is the average volume of the proteins attached to the particle. Alternatively, N can be derived from the expression:

$$N=0.65((r_2^3-r_1^3)/r_p^3)$$

where $r_p$ is the radius of the protein. Typically, the ionic conjugate includes between about 1 to about 25; preferably about 5 to about 15; and most preferably about 5 to about 10 proteins electrostatically attached to an inorganic particle having a diameter of about 19 Å.

In other embodiments, the inorganic particle can include an outer shell made up of either a) an organic shell, b) a thin silica layer, c) a combination of a and b. The organic shell can be monodentate or multidentate relative to the surface of the inorganic particles. The organic shell may also be polymerized around the particle.

The outer shell can be functionalized with groups that can self-assemble to biological moieties that have been either attached to the biological moiety, self-assemble to the moiety itself, or self-assemble to a synthetic molecule which then binds specifically to a biological moiety. The self-assembly process may be an electrostatic interaction with the surface group. The self-assembly can be through hydrogen bonding or through hydrophobic interactions.

Without further elaboration, it is believed that one skilled in the art can, based on the description herein, utilize the present invention to its fullest extent. The following specific examples, which describe syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

Synthesis of CdSe—ZnS-Lipoic Acid Nanoparticles:

Linking groups used to make semiconducting nanoparticles water soluble are attached to the surface of the semiconducting particle by exchanging trioctylphosphine (TOP)/trioctlyphosphineoxide (TOPO) groups on the surface of the particles with the desired linking group. A dihydrolipoic acid linking group was prepared by reducing commercially available lipoic acid (also called thioctic acid) purchased from Aldrich as a powder, with sodium borohydride ($NaBH_4$). See the procedure in A. F. Wagner, J. Organic Chemistry, 1956, 5079–81. The dihydrolipoic acid linking group increases the stability of the particle such that the modified particles can be used at much more dilute conditions. The procedure for exchanging the surface groups of the particles procedure is described below.

A volume of semiconducting nanoparticles (CdSe—ZnS) prepared using the synthesis route based on growth and annealing of organometallic compounds at high temperature (See Dabbousi et al.), was taken from the growth solution and precipitated by the addition of methanol. The nanoparticles included a ZnS-overcoating (5–7 monolayers). The isolated precipitate was then redispersed in a minimum volume of approximately 1:10 solution of butanol:hexane. Again, the semiconducting nanoparticles are crashed out by the addition of methanol. The procedure of precipitating, redispersing, and precipitating was repeated 2–3 times, until most of the TOP/TOPT groups on the surface of the particle were removed. A ten to twenty fold excess (by weight) of the desired linking group was added to the moist precipitate. The mixture was placed in an oil bath (around 60–80° C.) and stirred for approx. 3–12 hours. The group exchange procedure was stopped by removing the mixture from the oil bath. The mixture was diluted by adding a small amount of DMF (for approximately 200 mg of the desired linking group, 100–200 μl of DMF is sufficient). Separately, another solution with a slight molar excess (1.5:1) of potassium t-butoxide in a 1:10 volume of DMF:$H_2O$ is prepared and added to the semiconducting particle/DMF solution prepared above to protonate the lipoic acid groups. A whitish precipitate resulted, which was separated from the rest of the solution by centrifugation. The precipitate was readily dispersed in water. The nanocrystal dispersion was purified (from excess potassium t-butoxide and DMF) by concentrating from dilute solutions using an ultra-free centrifugal filtration device (from Millipore with cut off at ~50,000 daltons), and redispersing in water. Repeating the operation 3 to 4 times provides clean (a purity of ~95% or better) and stable dispersions in water, which have emission characteristics of the nanocrystals and a PL yield of ~15–20%.

In other synthetic schemes the base, tetramethylammonium hydroxide can be substituted for potassium t-butoxide in DMF. The former base though can be stored under air, whilst the latter needs to be kept in an inert atmosphere. The dihydrolipoic acid works best if it totally clear. If the reduction lipoic acid to produce dihydrolipoic acid is not complete, a yellow coloration of the solution will be evident. The yellow solution can be distilled (distills at 140° C. under vacuum) to yield a clear solution of dihydrolipoic acid.

Cloning and preparation of MBP-Basic Zipper Proteins Background references:

1) For MBP dimer expression in bacteria:

"Engineering the quaternary structure of an exported protein with a leucine zipper," Blondel, A. and Bedouelle, H (1991) Protein Eng. 4(4): 457–61.

2) For heterodimer formation via expressed recombinant proteins:

"A general method of facilitating heterodimeric pairing between proteins: application to expression of alpha and beta T-cell receptor extracellular segments," Chang, H. C., Bao, Z., Yao, Y., Tse, A. G., Goyarts, E. C., Madsen, M., Kawasaki, E., Brauer, P. P., Sachettini, J. C., Nathenson, S. G. et al. (1994) Proc. Natl. Acad. Sci. USA 91(24): 11408–11412.

3) For design and basic characterization of the leucine zippers used in this work:

"Peptide Velcro: design of a heterodimeric coiled coil," O'Shea, E. K., Lumb, K., and Kim, P. S. (1993) Current Biology 3(10): 658–667.

4) For a description of bioconjugates:

"Bioconjugation of Highly Luminescent Colloidal CdSe—ZnS Quantum Dots with an Engineered Two-Domain Recombinant Protein," H. Mattoussi et al. (2001) Phys. Stat. Sol. (b), 224(1): 277–283.

5) For a description of bioconjugates:

"Self-Assembly of CdSe—ZnS Quantum Dot Bioconjugates Using an Engineered Recombinant Protein," H. Mattoussi et al. (2001) J. Am. Chem. Soc., 122: 12142–12150.

Preparation of the Basic (Positively Charged) Leucine Zipper Gene

Two DNA oligonucleotide primers were synthesized to anneal to the 5' and 3' ends of the basic leucine zipper in the PCRIIBasic plasmid supplied by Chang et al.

Primer 1: 5'-TGCGGTGGCTCAGCTCAGTTG-3'  (SEQ ID NO:1)

Primer 2: 5'-GCTCTAGATTAATCCCCACCCTGGGCGAGTTTC-3'  (SEQ ID NO:2)

Using PCR, the basic zipper was amplified using primers 1 and 2 and pfu polymerase to produce a DNA fragment of approximately 120 bp coding for the basic zipper and with termini suitable for processing prior to insertion 3' of the MalE gene and coding for a stop codon and a unique cysteine residue 5' of the zipper sequence for eventual covalent dimer formation in the expressed fusion protein. Processing of the amplified zipper-encoding fragment was achieved by digesting a portion of the DNA with restriction endonuclease XbaI to provide an appropriately overlapping 3' terminus for the subsequent cloning step. The 5' end of the PCR fragment was designed to be blunt ended, so no additional processing was required prior to the next step.

Cloning of the Leucine Zipper Gene onto the C-Terminal Coding Sequence for MBP

The prepared DNA fragment was then ligated enzymatically into the commercial vector pMal-c2 (New England Biolabs) that had been processed with the restriction endonucleases XmnI and XbaI; these enzyme cleavage sites in the DNA vector provided the 5' blunt and 3' overlapping sequences required for successful ligation of the prepared basic leucine zipper containing fragment prepared as described. After transformation of E. coli DH5" with ligation product and obtaining ampicillin resistant bacterial colonies, several colonies were tested for presence of the desired inserted basic leucine zipper DNA by colony PCR using DNA oligonucleotide primers flanking the vector cloning sites. Several positive colonies were chosen for amplification by overnight growth on a small scale, followed by preparation of small amounts of pMal-Basic Zipper DNA.

Expression of the MBP-Basic Zipper Protein in Bacteria

Several candidate plasmids from the above cloning procedure were tested for the ability to express the desired fusion protein in the DH5" host bacterial strain as evaluated by small-scale cell culture (10 ml) and SDS gel electrophoresis of IPTG-induced expression product. Out of several successful clones, one was selected to carry out DNA sequencing to verify the accuracy of the DNA sequence, for further expression studies, and ultimately for larger scale expression work. The correct expected DNA sequence for the selected clone was verified by the MGIF sequencing facility at the University of Georgia.

Additional small-scale expression studies in various bacterial strains were subsequently conducted to optimize production of the fusion protein. E. coli BL21, a Ion protease deficient strain, proved to be suitable for expression of the protein.

Appending a (His)6 (Hexahistidine) Peptide onto the C-Terminus of the Fusion Protein In order to provide additional flexibility in preparation and purification of this and other similar fusion proteins, DNA coding for a hexahistidine peptide sequence was appended onto the 3'-end of the pMal-basic Zipper sequence. Preparing this construct required synthesis of a new 3' primer used together with primer 1 (above) to allow amplification of a basic zipper DNA fragment lacking the codon for translation termination that was implanted in the initial construct described above: Primer 3:5'-GCTCTAGATGAATCCCCACCCTGGGCGAGTTTC-3' (SEQ ID NO:3).

Following exactly the procedure described above, an intermediate construct was made that was identical to the pMal-Basic Zipper except for the lack of a stop codon 3' of the leucine zipper. DNA coding this intermediate construct was cleaved with restriction endonucleases XbaI and PstI, and the following synthetically prepared duplex DNA was enzymatically ligated into these sites:

5'-CTAGCGGTCACCACCACCACCACCACTGACTGCA-3'  (SEQ ID NO:4)

3'-GCCAGTGGTGGTGGTGGTGGTGACTG-5'.  (SEQ ID NO:5)

After transformation of E. coli DH5" with ligation products of the vector and the indicated insert DNA, colony PCR analysis once more used to find clones coding for MBP followed in tandem by the basic leucine zipper sequence, the hexahistidine sequence and a translational stop codon. Expression in E. coli BL21 was again found to yield satisfactory amounts and quality of protein for larger scale work.

Cell Culture of Either MBP-Basic Zipper or MBP-Basic Zipper-(His)6 Protein

A single colony of freshly transformed E. coli BL21 was transferred into 10 ml Luria Broth (LB) containing 100 µg/ml carbenicillin and the culture was shaken at 37° C. overnight (approximately 15 hr). 2.0 ml of this overnight culture was transferred into 1 liter of LB containing 50 µg/ml carbenicillin and 2 grams glucose. After growing to an optical density of 0.6 at 37° C., the flask containing the cell culture was transferred to shaking at 30° C. for 15 min prior to adding IPTG (isopropylthiogalactopyranoside) to a final concentration of 1 mM. After 2 hr shaking at this temperature, the cells were sedimented at 4° C. by centrifugation. The resulting cell pellet was quick frozen in powdered dry ice and stored at −80° C. until thawing for purification.

Purification of MBP-Basic Zipper-(His)6 from 1 Liter of Cell Culture

Lysis buffer (35 ml of 50 mM HEPES, 0.3 M NaCl, 5 mM imidazole, pH 7.9 containing one tablet of Boehringer EDTA-free protease inhibitor cocktail) was added to the tube containing the thawing pellet freshly removed from −80° C. storage. After complete resuspension on ice, the cells were lysed by sonication for 5×1 minute in ice water. The lysed cells were centrifuged at 16,000 RPM at 4° C. for 30 min. After the crude supernatant was passed through a 0.8/0.2 micron dual stage syringe ultrafilter, 15 ml of a 50% suspension of NiNta metal chelating resin (Qiagen) equilibrated with lysis buffer was added, and the tube tumbled at 4° C. for 1 hr. The resin and bound protein was briefly centrifuged and the supernatant discarded; the resin was then washed 2× with 40 ml lysis buffer. The washed resin was poured into a 1.5 cm diameter glass chromatography at 4° C., and 50 ml lysis buffer (sans protease inhibitors) was passed over the column at 0.8 ml/min, followed by 90 ml wash buffer (50 mM HEPES, 0.3 M NaCl, 20 mM imidazole, pH 7.9). The product is eluted from the washed column with elute buffer (50 mM HEPES, 0.3 M NaCl, 250 mM imidazole, pH 7.4). Pooled fractions containing protein were then applied to a 25 ml packed bed (2 cm diameter) column of immobilized amylose (4° C.) previously equilibrated with 50 mM HEPES, 0.1 M NaCl, pH 7.4 at ca. 1 ml/min. The column was washed with 100 ml of the above buffer, then the protein was eluted with this buffer containing 10 mM maltose. Collected fractions containing purified protein were pooled and passed through a sterile 0.45 micron syringe filter and stored at 4° C. Purified protein was analyzed by SDS gel electrophoresis+/−dithiothreitol reducing agent (15 mg/ml in boiled samples) to evaluate the degree of dimer formation.

Maltose Binding Protein Ionic Conjugate

The MBP-leucine zipper fusion protein was electrostatically attached to the CdSe(core)-ZnS(overcoat)-dihydrolipoic acid modified semiconducting particles by mixing the fusion protein and inorganic particles in borate buffered solutions at pH ~8–9. A pH greater than about 7 is most suitable for protein manipulation by preserving the nanocrystal solubility and imparting negative surface charge coverage. Simple addition of the MBP-leucine zipper fusion protein to a solution containing a fixed amount of nanocrystals in buffered solution yielded ionic bio-conjugates free of aggregates, irrespective of the mole ratio of inorganic particles to proteins. Typically, the ratio of inorganic particles to proteins is between 1 and 10. The inorganic particles had an average diameter of about 19 Å.

Figure 5:
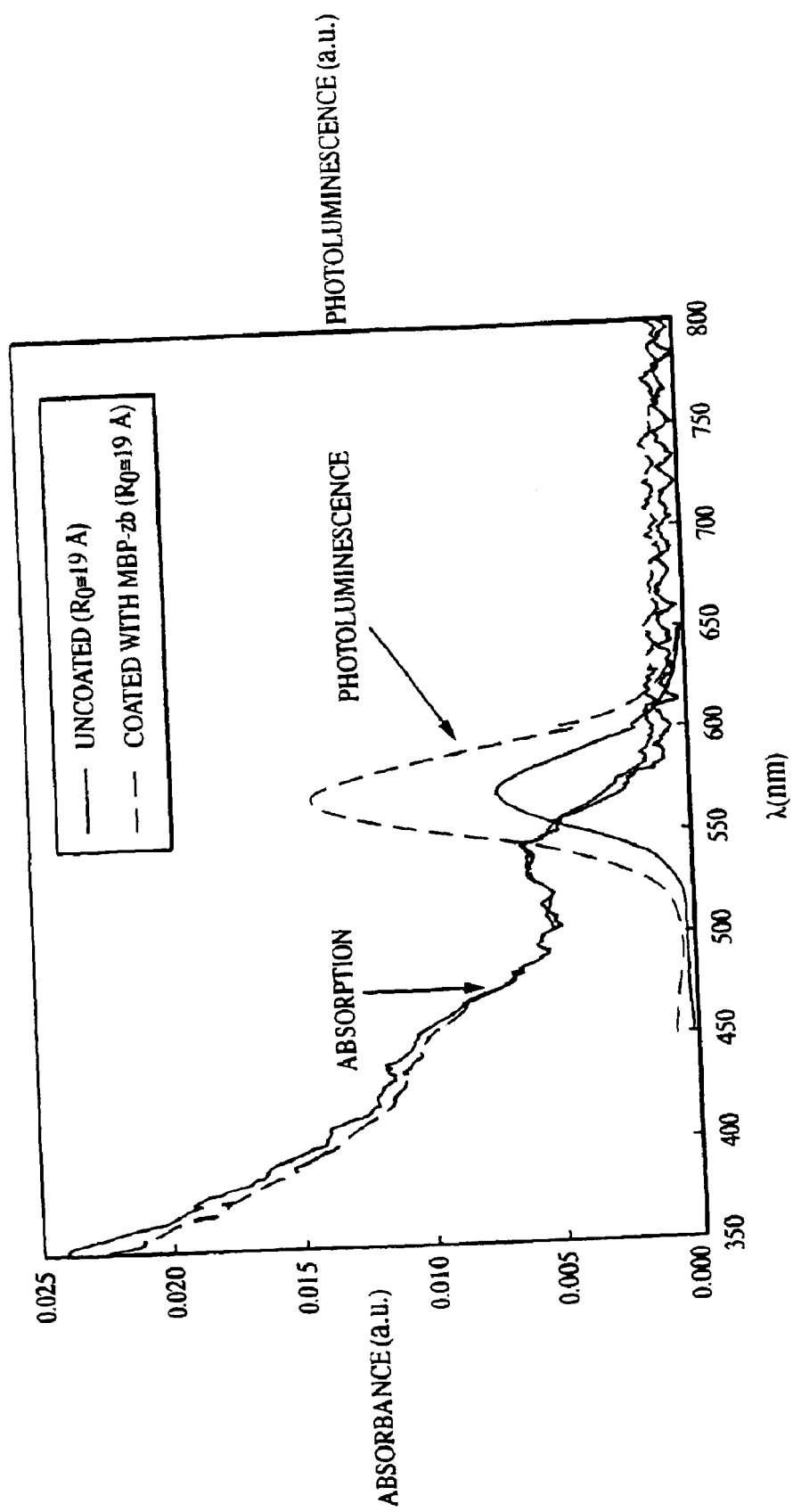
FIG. 5 includes absorption and photoluminescence spectra of solutions containing CdSe—ZnS semiconducting particles and CdSe—ZnS semiconducting particles coated with MBP-zipper.

The advantage of surface modification using the present method is its simplicity and versatility. It is only necessary to add the fusion protein to the particles to coat, and the desired protein attaches to the surface nearly instantaneously. Furthermore, in some instances coating of the inorganic particles with the biological moieties results in enhancement of the photoluminescence yield. FIG. 5 shows that particles coated with the MBP-zipper protein have approximately a three-fold increase in luminescence intensity relative to particles which are not electrostatically associated with a biological moiety.

Figure 6C:
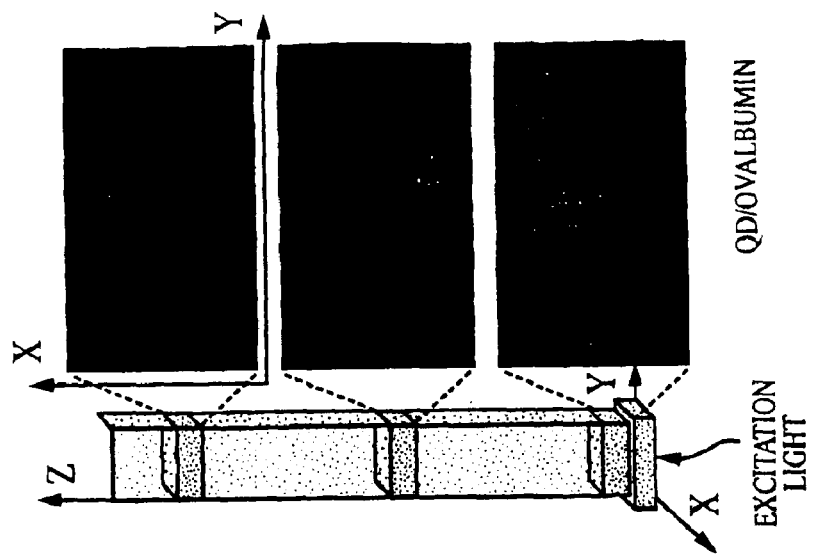
FIGS. 6A–6C shows cross-sections (~15 mm thick each) of thin film solutions of CdSe—ZnS nanoparticles coated with MBP-leucine zipper recombinant proteins (a); uncoated CdSe—ZnS nanoparticles (b); CdSe—ZnS nanoparticles coated with IgG using a covalent cross-linking agent EDAC (c).
Figure 6B:
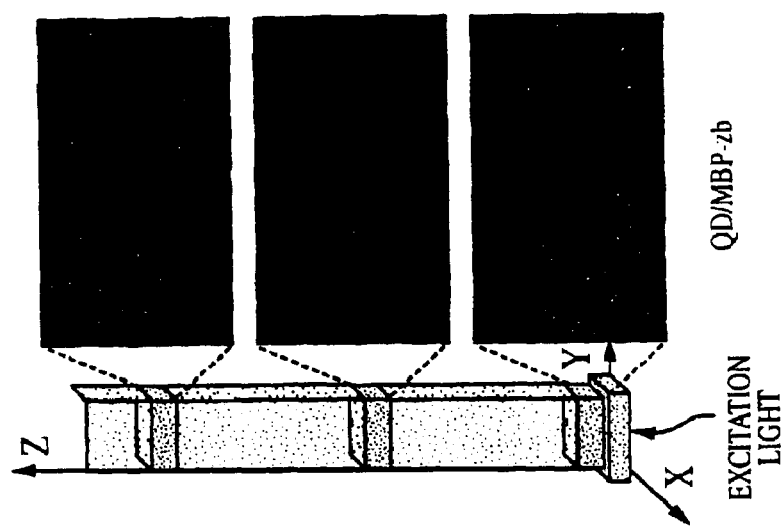
Figure 6A:
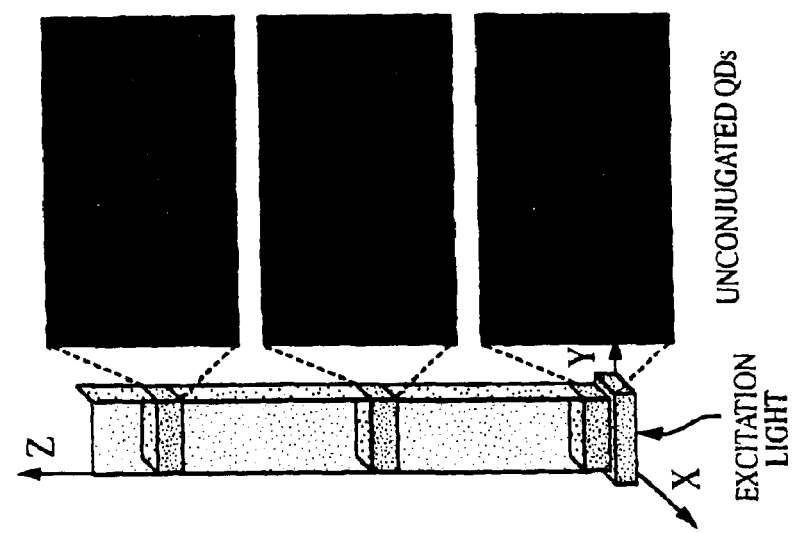

The MBP-zipper coated nanocrystals (and particles) prepared via noncovalent cross-linking were also examined using fluorescence confocal microscopy imaging. FIGS. 6A–6C show cross-sectional images using a laser scanning confocal microscope of solutions of MBP-Zipper bound to nanocrystals (core-overcoat with 19 Å core radius), along with an image of a sample of the same particles covalently cross-linked to ovalbumin via such as 1-ethyl-3-(3-dimethylaminopropyl) carbodiimide hydrochloride (EDAC or EDC). Covalent cross-linking procedure are discussed in "Semiconductor Nanocrystals as Fluorescent Biological Labels," Science 281, 2013–2016 (1998), by Bruchez, Jr. et al.; "Quantum Dot Bioconjugates for Ultrasensitive Nonisotopic Detection," Science 281, 2016–2018, by W. C. W. Chan, and S. Nie; and references cited therein. Significant aggregates (that manifest in a the appearance of constellation-like features) were formed when using the covalent method (FIG. 6C), whereas ionic conjugates of inorganic particles coated with the MBP-zipper appeared identical to uncoated material (See FIGS. 6A and 6B). The emission recorded in FIGS. 6A and 6B results from single particles and is characteristic of a stable and aggregation-free solutions. Additionally, the photoluminescence of the inorganic particles coated with the MBP-zipper (FIG. 6A) was increased relative to uncoated inorganic particles (FIG. 6B) for thin films containing the comparable concentration of particles. For each image, the solution of ionic bioconjugates was excited at 488 nm, i.e., below the location of the first absorption peak of the nanoparticles. Appropriate filters were used to block out the excitation signal. Images of nanoparticles coated with ovalbumin using the covalent (EDAC) binding approach were also recorded along with images of pure nanoparticle (protein-free) and nanoparticles complexed to fusion proteins. Each image represents very thin slices (~15 micron thick and an area of 150×100 micron$^2$ each) along the laser path (exciting signal traveling vertically). The last images in the bottom of the figure represent the cut adjacent to the support surface (bottom of the optical dish). The green bright spots on the images represent luminescence emission from individual nanoparticles dispersed in the solution film. The results described above indicate that the present coating approach is effective in providing aggregation-free (even at very small scales) nanocrystal-protein bioconjugates. The samples are stable over a long period of time (months). The aggregates (FIG. 6C) precipitate to the bottom of the sample by gravity, and leave non-reacted particles floating in the solution, which may give the false impression that covalently coated particles are stable and do not encounter large scale aggregation. Aggregation was even more pronounced in solutions where IgG is attached to the nanocrystals via EDAC (data not shown).

Figure 7B:
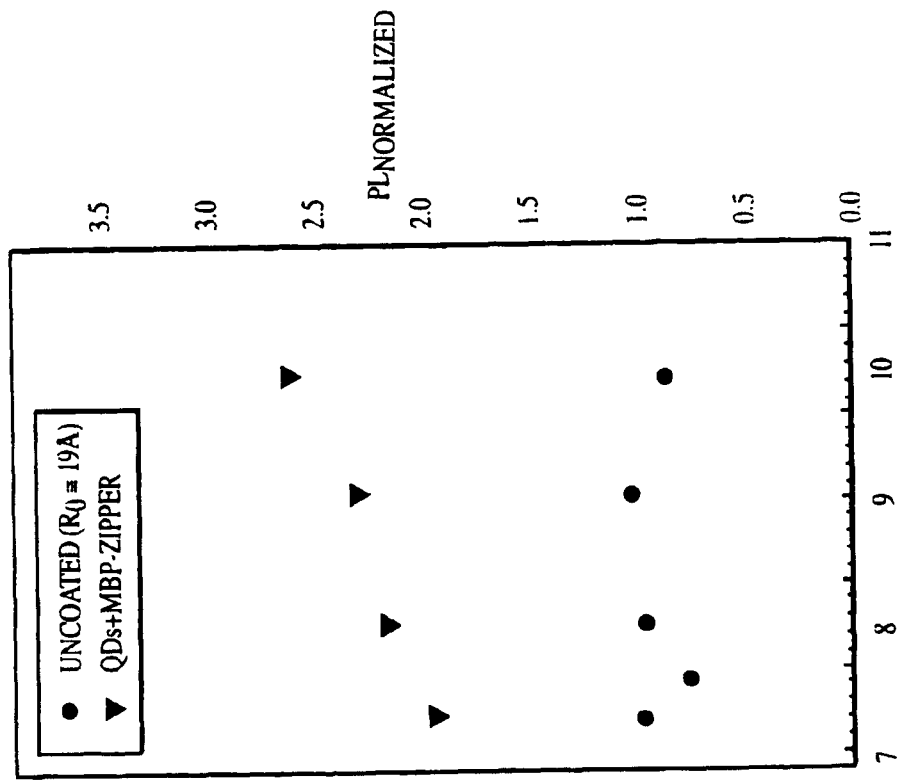
FIG. 7B is a graph of photoluminescence as a function of pH. Note that like reference symbols in the various drawings indicate like elements.
Figure 7A:
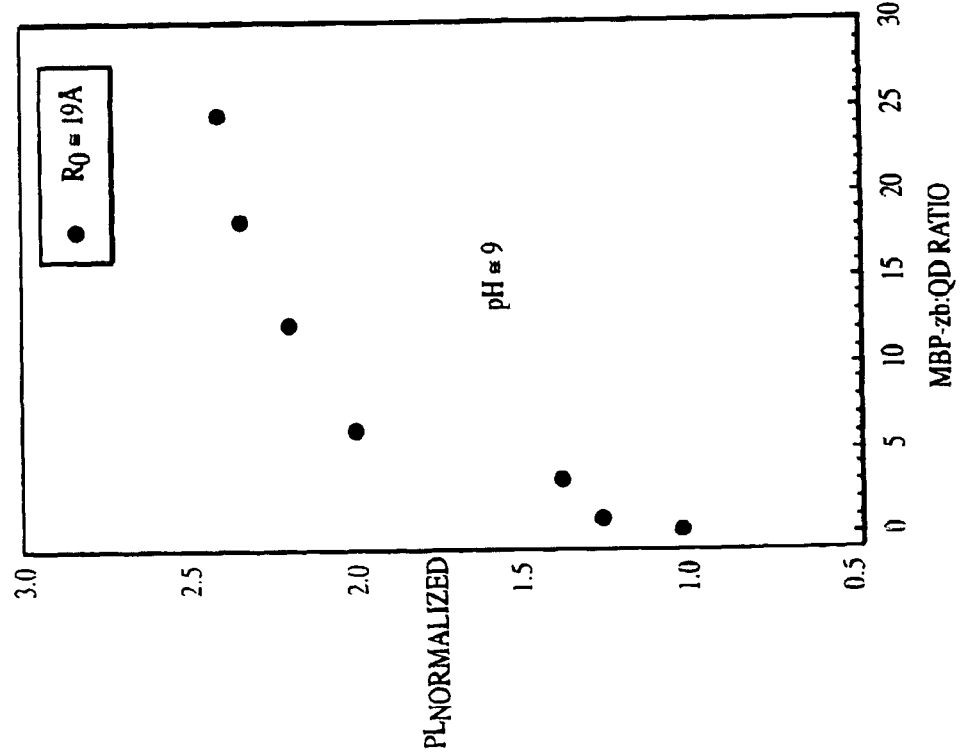
FIG. 7A is a graph of photoluminescence as a function of the number of electrostatically bound proteins.

Referring to FIGS. 7A and 7B, the effects of pH and the number of protein on the nanoparticle were tested. At pH of about 9, the photoluminescence increases as the number of fusion proteins electrostatically attached to the nanoparticle is increased. At a constant number of proteins complexed to the nanoparticles, the photoluminescence increased with increasing pH.

In a subsequent experiment, the bioactivity of the ionic conjugates including the MBP was tested by passing the ionic conjugates through a column of amylose functionalized resins. The ionic conjugates bound to the resin as MBP interacted with amylose. Thus, the ionic conjugates maintained their bioactivity. Ionic conjugates bound to the amylose functionalized resins were released by washing the column with a maltose solution.

Cloning and Preparation of G-Basic Zipper Proteins

The coding sequence for the IgG binding b2 sub-domain of streptococcal protein G (PG) was cloned and expressed in the *E.coli* cloning vector pBad/HisB (an inducible expression vector from Invitrogen). The linker plus the leucine zipper tail were inserted downstream at the site 3' away from the PG. In addition, a polyhistidine short chain (hexahistidine) was attached to the end of the leucine tail to facilitate purification of the final product. These successive gene manipulations provided a fusion streptococcal protein G that has an IgG b2 binding sub-domain and a leucine zipper charged tail, which plays a major role in the present coating scheme.

Ionic conjugates including semiconducting nanoparticles (CdSe—ZnS) coated with protein G-zipper were synthesized via the method described above. However, the ratio of inorganic particles to biomolecules, typically, is less than the ratio of MBP-proteins to inorganic particles.

The resulting ionic bioconjugates were passed through a column containing resins functionalized with IgG and allowed to react for approximately 15 minutes. Washing the column with pure buffer solution resulted in the release of negligible amounts of ionic bio-conjugates. The functionalized column retained approximately 95–98% of the ionic bioconjugates. The percentage of ionic conjugates contained within the column was determined by monitoring the effluent from the column for luminescence indicative of the semiconducting particles. These results imply that protein G-zipper molecules bind to the inorganic particles.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising:
   a semiconductor nanocrystal,
   a linking group which has a distal end and a proximal end, the distal end being bound to an outer surface of the semiconductor nanocrystal and the proximal end comprising a first charged or ionizable moiety, wherein the distal end comprises S, N, P, O, or O=P;
   the first charged or ionizable moiety is selected from the group consisting of a hydroxide, an alkoxide, a carboxylate, a sulfonate, a phosphate, a phosphonate and a quaternary ammonium; and
   the distal and proximal ends are connected by a spacer or a bond, and
   a fusion protein comprising a second charged or ionizable moiety, wherein the first and second charged or ionizable moieties electrostatically associate the semiconductor nanocrystal with the fusion protein to form an ionic conjugate.

2. The composition of claim 1, wherein the spacer is selected from a branched or unbranched C2–C100 alkylene, a branched or unbranched C2–C100 alkenylene, a branched or unbranched C2–C100 heterolkenylene, cycloalkyl, cycloalkenyl, cycloalkynyl, heterocyclic, aryl, and heteroaryl.

3. The composition of claim 1, wherein the semiconductor nanocrystal comprises a first semiconductor material, and wherein the first semiconductor material is a Group II-VI compound.

4. The composition of claim 1, wherein the semiconductor nanocrystal is further bound to a plurality of linking groups each independently comprising a third charged or ionizable moiety.

5. The composition of claim 4 further comprising a plurality of macromolecules, each of the macromolecules comprising a fourth charged or ionizable moiety, wherein the plurality of macromolecules are associated with the semiconductor nanocrystal via electrostatic interaction with the plurality of semiconductor nanocrystal linking groups.

6. The composition of claim 1, wherein the second charged or ionizable moiety is selected from the group consisting of a hydroxide, an alkoxide, a carboxylate, a sulfonate, a phosphate, a phosphonate and a quaternary ammonium.

7. The composition of claim 1, wherein the linking group has the formula:

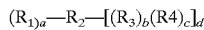

wherein
$R_1$ is selected from the group consisting of C1–C100 heteroalkyl, C2–C100 heteroalkenyl, heteroalkynyl, —OR, —SH, —NHR, —NR'R", —N(O)HR, —N(O)R'R", —PHR, —PR'R", —P(NR'R")NR'R", —P(O)R'R", —P(O)(NR'R")NR'R", —P(O)(OR')OR", —P(O)OR, —P(O)NR'R", —P(S)(OR')OR", and —P(S)OR, wherein R, R', R" are independently selected from the group consisting of H, a branched or unbranched C1–C100 alkyl, a branched or unbranched C2–C100 alkenyl, a branched or unbranched C2–C100 alkynyl, a branched or unbranched C1–C100 heteroalkyl, a branched or unbranched C2–C100 heteroalkenyl, a branched or unbranched C2–C100 heteroalkynyl, with the proviso that when a is greater than 1 the $R_1$ groups can be attached to the $R_2$ or $R_3$ groups at the same or different atoms within those groups, the $R_1$ groups can be the same or different, or the $R_1$ groups can form a six, seven, eight, nine, or ten membered cycloalkyl, cycloalkenyl, heterocyclic, aryl, heteroaryl, or a six- to thirty-membered crown ether or heterocrown ether, $R_2$ is selected from a bond, a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_3$ is selected from a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_4$ is selected from the group consisting of hydrogen, a carboxylate, a thiocarboxylate, an amide, a hydrazine, a sulfonate, a sulfoxide, a sulfone, a sulfite, a phosphate, a phosphonate, a phosphonimum ion, an alcohol, a thiol, an amine, an ammonium, an alkyl ammonium, a nitrate; and a is 1 to 40, b is 0 to 3, c is 1 to 30, d is 1 to 3, and when d is 2 or 3 the $R_3$ groups can be the same or different or can be linked together to form a five to ten members cycloalkyl, cycloalkenyl, heterocyclic, aryl, or heteroaryl.

8. The composition of claim 1, wherein the linking group has the formula

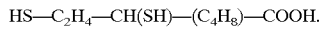

9. The composition of claim 1, wherein the second charged or ionizable moiety is a leucine zipper.

10. The composition of claim 1, wherein the second charged or ionizable moiety is polyaspartate.

11. The composition of claim 1, wherein the fusion protein includes a maltose binding protein.

12. The composition of claim 1, wherein the fusion includes an immunoglobulin G binding protein.

13. The composition of claim 1, wherein the first semiconductor material is CdSe.

14. The composition of claim 13, wherein the first semiconductor material is overcoated with a second semiconductor material.

15. A method of forming an ionic conjugate, comprising:

providing a semiconductor nanocrystal with a linking group having a distal end and a proximal end, wherein the distal end is bound to an outer surface of the semiconductor nanocrystal, and the proximal end comprises a first charged or ionizable moiety, and wherein the distal end comprises S, N, P, O, or O=P, the first charged or ionizable moiety is selected from the group consisting of a hydroxide, an alkoxide, a carboxylate, a sulfonate, a phosphate, a phosphonate and a quaternary ammonium, and the distal and proximal ends are connected by a spacer or a bond; and contacting a fusion protein having a second charged or ionizable moiety with the semiconductor nanocrystal, wherein the first and second charged or ionizable moieties electrostatically associate the semiconductor nanocrystal with the fusion protein to form an ionic conjugate.

16. The method of claim 15, wherein the first semiconductor material is overcoated with a second semiconductor material.

17. The method of claim 15, wherein the spacer is selected from a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl.

18. The method of claim 15, wherein the semiconductor nanocrystal comprises a first semiconductor material, wherein the first semiconductor material is a Group II-VI compound.

19. The method of claim 18, wherein the first semiconductor material is CdSe.

20. The method of claim 19, wherein the first semiconductor material is overcoated with a second semiconductor material.

21. The method of claim 15, wherein the semiconductor nanocrystal is further bound to a plurality of linking groups each independently comprising a third charged or ionizable moiety.

22. The method of claim 21, further comprising a plurality of macromolecules, each of the macromolecules comprising a fourth charged or ionizable moiety, wherein the plurality of macromolecules are associated with the semiconductor nanocrystal via electrostatic interaction with the plurality of linking groups.

23. The method of claim 15, wherein the second charged or ionizable moiety is selected from the group consisting of a hydroxide, an alkoxide, a carboxylate, a sulfonate, a phosphate, a phosphonate and a quaternary ammonium.

24. The method of claim 15, wherein the linking group has the formula:

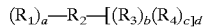

wherein $R_1$ is selected from the group consisting of C1–C100 heteroalkyl, C2–C100 heteroalkenyl, heteroalkynyl, —OR, —SH, —NHR, —NR'R", —N(O)HR, —N(O)R'R", —PHR, —PR'R", —P(NR'R")NR'R", P(O)R'R", P(O)(NR'R")NR'R", —P(O)(OR')OR", P(O)OR, P(O)NR'R", —P(S)(OR')OR", and P(S)OR, wherein R, R', R" are independently selected from the group consisting of H, a branched or unbranched C1–C100 alkyl, a branched or unbranched C2–C100 alkenyl, a branched or unbranched C2–C100 alkynyl, a branched or unbranched C1–C100 heteroalkyl, a branched or unbranched C2–C100 heteroalkenyl, a branched or branched C2–C100 heteroalkynyl, with the proviso that when a is greater than 1 the $R_1$ group can be attached to the $R_2$ or $R_3$ groups at the same or different atoms within those groups, the $R_1$ groups can be the same or different, or the $R_1$ groups can form a six, seven, eight, nine, or ten membered cycloalkyl, cycloalkenyl, heterocyclic, aryl, heteroaryl, or a six- to thirty-membered crown ether or heterocrown ether;

$R_2$ is selected from a bond (i.e., $R_2$ is absent in which case $R_1$ attaches to $R_3$), a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_3$ is selected from a branched or unbranched C2–C100 alkylene, a branched or unbranched C2–C100 alkenylene, a branched or unbranched C2–C100 heteroalkenylene, cycloalkyl, cycloalkenyl, cycloalkynyl, heterocyclic, aryl, and heteroaryl;

$R_4$ is selected from the group consisting of hydrogen, a carboxylate, a thiocarboxylate, and amid, an amine, a hydrazine, a sulfonate, a sulfoxide, a sulfone, a sulfite, a phosphate, a phosphonate, a phosphonium ion, an alcohol, a thiol, an amine, ammonium, an alkyl ammonium, a nitrate; and a is 1 to 4, b is 0 to 3, c is 1 to 3, d is 1 to 3, and when d is 2 or 3 the $R_3$ groups can be the same or different or can be linked together to form a five to ten members cycloalkyl, cycloalkenyl, heterocyclic, aryl, or heteroaryl.

25. The method of claim 15, wherein the linking group has the formula

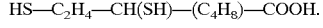

26. The method of claim 15, wherein the second charged or ionizable moiety is a leucine zipper.

27. The method of claim 15, wherein the second charged or ionizable moiety is polyaspartate.

28. The method of claim 15, wherein the fusion protein includes a maltose binding protein.

29. The method of claim 15, wherein the fusion protein includes an immunoglobulin G binding protein.

* * * * *

UNITED STATES PATENT AND TRADEMARK OFFICE
CERTIFICATE OF CORRECTION

| | | |
|---|---|---|
| PATENT NO. | : 6,921,496 B2 | Page 1 of 1 |
| APPLICATION NO. | : 09/811824 | |
| DATED | : July 26, 2005 | |
| INVENTOR(S) | : Anderson et al. | |

It is certified that error appears in the above-identified patent and that said Letters Patent is hereby corrected as shown below:

Col. 1 lines 10-15
In the section FEDERALLY SPONSORED RESEARCH OR DEVELOPMENT, the text "This invention was made with government support under Contract No. DMR-98-08941 from the National Science Foundation and Contract Nos. N0001499WX30470 and N0001400WX20094 from the Office of Naval Research. The government may have certain rights in the invention." should read -- This invention was made with Government support under Grant No. DMR9871996, awarded by the National Science Foundation. The Government has certain rights in this invention. --

Signed and Sealed this
Tenth Day of May, 2011

David J. Kappos
*Director of the United States Patent and Trademark Office*

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 1
tgcggtggct cagctcagtt g                                              21

<210> SEQ ID NO 2
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 2
gctctagatt aatccccacc ctgggcgagt ttc                                 33

<210> SEQ ID NO 3
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 3
gctctagatg aatccccacc ctgggcgagt ttc                                 33

<210> SEQ ID NO 4
<211> LENGTH: 34
<212> TYPE: DNA
<213> ORGANISM: Artificial Sequence
<220> FEATURE:
<223> OTHER INFORMATION: Synthetically generated primer

<400> SEQUENCE: 4
ctagcggtca ccaccaccac caccactgac tgca                                34

<210> SEQ ID NO 5
<211> LENGTH: 26
<212> TYPE: DNA
<213> ORGANISM: Artificial Sequence
<220> FEATURE:
<223> OTHER INFORMATION: Synthetically generated primer

<400> SEQUENCE: 5
gtcagtggtg gtggtggtgg tgaccg                                         26

<210> SEQ ID NO 6
<211> LENGTH: 105
<212> TYPE: DNA
<213> ORGANISM: Artificial Sequence
<220> FEATURE:
<223> OTHER INFORMATION: Synthetically generated primer

<400> SEQUENCE: 6
tcagctcagt tgaaaaaaaa attgcaagca ctgaagaaaa agaacgctca gctgaagtgg    60
aaacttcaag ccgtcaagaa gaaactcgcc cagggtgggg attca                   105

```
-continued
<210> SEQ ID NO 7
<211> LENGTH: 35
<212> TYPE: PRT
<213> ORGANISM: Artificial Sequence
<220> FEATURE:
<223> OTHER INFORMATION: Synthetically generated peptide

<400> SEQUENCE: 7

Ser Ala Gln Leu Lys Lys Lys Leu Gln Ala Leu Lys Lys Lys Asn Ala
 1               5                  10                  15

Gln Leu Lys Trp Lys Leu Gln Ala Leu Lys Lys Lys Leu Ala Gln Gly
            20                  25                  30

Gly Asp Ser
         35
```